(12) United States Patent
Ryu

(10) Patent No.: US 11,187,655 B2
(45) Date of Patent: Nov. 30, 2021

(54) COMPACT GAS SENSORS

(71) Applicant: SENSERA, INC., Woburn, MA (US)

(72) Inventor: Jaeseok Ryu, Carlisle, MA (US)

(73) Assignee: SENSERA, INC., Woburn, MA (US)

( * ) Notice: Subject to any disclaimer, the term of this patent is extended or adjusted under 35 U.S.C. 154(b) by 0 days.

(21) Appl. No.: 16/414,599

(22) Filed: May 16, 2019

(65) Prior Publication Data
US 2019/0353593 A1 Nov. 21, 2019

Related U.S. Application Data

(60) Provisional application No. 62/810,120, filed on Feb. 25, 2019, provisional application No. 62/672,354, filed on May 16, 2018.

(51) Int. Cl.
*G01N 21/59* (2006.01)
*G01N 21/3504* (2014.01)
*G01N 33/00* (2006.01)

(52) U.S. Cl.
CPC ......... *G01N 21/59* (2013.01); *G01N 21/3504* (2013.01); *G01N 33/0009* (2013.01); *G01N 2021/5903* (2013.01)

(58) Field of Classification Search
CPC ............... G01N 21/59; G01N 21/3504; G01N 33/0009; G01N 2021/5903; G01N 21/39; G01N 21/05; G01N 21/031; G01N 21/274; G01N 21/31; G01N 33/497; G01N 2021/1793; G01N 21/65; G01N 21/658;

(Continued)

(56) References Cited

U.S. PATENT DOCUMENTS 3,676,005 A * 7/1972 Chance ................... G01J 3/427
356/320
3,787,121 A * 1/1974 Lowy ..................... G01J 3/0232
356/73

(Continued)

FOREIGN PATENT DOCUMENTS

| DE | 102018203100 B3 | 3/2019 |
| EP | 1612540 A1 | 1/2006 |
| WO | 2019/020937 A1 | 1/2019 |

OTHER PUBLICATIONS

Barritault et al., Mid-IR source based on a free-standing microhotplate for autonomous CO2 sensing in indoor applications. Sensors and Actuators A: Physical. Dec. 2011,172(2):379-385.

(Continued)

*Primary Examiner* — Mohamed K Amara
(74) *Attorney, Agent, or Firm* — McCarter & English, LLP

(57) ABSTRACT

Systems and methods herein provide low power non-dispersive infrared (NDIR) gas sensors. The gas sensors comprise a thin film plasmonic light source that produces a time modulated parallel light beam at multiple selected wavelengths. The parallel light beam from the light source passes through a gas chamber without using focusing or collimating optical components. The gas sensors are continuously self-calibrated against environmental changes, such as temperatures and relative humidity, and aging. The gas sensors are suitable for use in hazardous environments because their low power and small thermal mass reduces the risk of explosion. The gas sensors can be integrated into conventional mobile device platforms.

24 Claims, 20 Drawing Sheets

(58) Field of Classification Search
CPC ......... G01N 33/57492; G01N 33/6896; G01N 30/6095; G01J 3/42; G01J 3/02; G01J 3/10; G01J 3/433; G01J 3/427; G01J 3/44; A61K 2039/505; B82Y 30/00; B82Y 20/00; B82Y 15/00; B82Y 40/00; B82Y 10/00; B82Y 5/00; B82Y 35/00; B82Y 25/00; G02B 5/008; G02B 6/1226; G02B 6/1225; G02B 5/1809; G02B 1/002; G02B 6/12007; G02B 26/001; G02B 2207/101; G02B 1/005; G02B 6/122; G02B 6/34; G02B 5/201; G02B 2006/12138; G02B 6/43; G02B 26/0833; G02B 21/32; G02F 2203/10; G02F 2202/36; G02F 1/0126

See application file for complete search history.

(56) References Cited

U.S. PATENT DOCUMENTS

| | | | | |
|---|---|---|---|---|
| 4,323,309 | A * | 4/1982 | Akitomo | G01J 3/42 356/319 |
| 5,559,728 | A * | 9/1996 | Kowalski | G01N 21/274 250/252.1 |
| 5,869,749 | A | 2/1999 | Bonne et al. | |
| 6,469,303 | B1 | 10/2002 | Sun et al. | |
| 6,756,594 | B2 | 6/2004 | George et al. | |
| 6,815,211 | B1 * | 11/2004 | Blazewicz | A61B 5/0833 422/425 |
| 7,244,939 | B2 | 7/2007 | Stuttard | |
| 7,498,574 | B2 | 3/2009 | Puscasu et al. | |
| 7,741,625 | B2 | 6/2010 | Rogne et al. | |
| 7,825,380 | B2 | 11/2010 | Puscasu et al. | |
| 7,843,379 | B2 | 11/2010 | Menzer et al. | |
| 8,492,737 | B2 | 7/2013 | Araci et al. | |
| 8,643,532 | B1 | 2/2014 | Puscasu et al. | |
| 9,007,687 | B2 | 4/2015 | Puscasu et al. | |
| 9,214,604 | B2 * | 12/2015 | Ali | H01L 33/34 |
| 9,513,204 | B2 * | 12/2016 | Paul | G01N 15/06 |
| 9,588,255 | B1 * | 3/2017 | Tassin | G02B 1/007 |
| 9,804,084 | B2 | 10/2017 | Kouznetsov et al. | |
| 9,909,926 | B2 | 3/2018 | Hopper et al. | |
| 9,983,292 | B2 | 5/2018 | Hach et al. | |
| 10,088,416 | B2 * | 10/2018 | Niiranen | G01N 21/39 |
| 10,365,416 | B2 * | 7/2019 | Zhan | G02B 5/1828 |
| 10,444,076 | B2 * | 10/2019 | Winger | G01J 5/10 |
| 2003/0081875 | A1 * | 5/2003 | Kochergin | G01N 21/7703 385/12 |
| 2004/0086423 | A1 * | 5/2004 | Wohlstadter | G01N 21/66 422/52 |
| 2009/0108726 | A1 | 4/2009 | Watanabe et al. | |
| 2011/0086676 | A1 * | 4/2011 | Choi | G01S 17/04 455/567 |
| 2012/0129269 | A1 * | 5/2012 | Choi | G01J 3/02 436/164 |
| 2012/0238035 | A1 * | 9/2012 | Geddes | B82Y 15/00 436/501 |
| 2012/0267532 | A1 | 10/2012 | Udrea et al. | |
| 2013/0148194 | A1 * | 6/2013 | Altug | G01N 21/554 359/350 |
| 2013/0208332 | A1 * | 8/2013 | Yu | H01Q 15/10 359/240 |
| 2013/0258332 | A1 * | 10/2013 | Iga | G01J 3/26 356/301 |
| 2014/0011844 | A1 | 1/2014 | Danishefsky et al. | |
| 2014/0061486 | A1 * | 3/2014 | Bao | G02B 1/02 250/370.01 |
| 2014/0085693 | A1 * | 3/2014 | Mosallaei | G02B 1/002 359/107 |
| 2014/0218738 | A1 * | 8/2014 | Bartoli | G01N 21/7703 356/450 |
| 2015/0049377 | A1 * | 2/2015 | Zheludev | G02B 5/008 359/244 |
| 2015/0153341 | A1 * | 6/2015 | Lee | B82Y 15/00 435/5 |
| 2015/0362641 | A1 * | 12/2015 | Boyraz | G02B 5/1861 359/350 |
| 2016/0091429 | A1 * | 3/2016 | Huber | H01S 3/302 356/301 |
| 2016/0099701 | A1 * | 4/2016 | Rinaldi | G01J 5/20 422/90 |
| 2016/0209271 | A1 * | 7/2016 | Rowlette | G01J 3/2803 |
| 2016/0282259 | A1 | 9/2016 | Kolb et al. | |
| 2016/0320531 | A1 * | 11/2016 | Kamali | G02B 5/0263 |
| 2017/0030773 | A1 * | 2/2017 | Han | G01J 3/0208 |
| 2017/0052118 | A1 * | 2/2017 | Loock | G01J 3/021 |
| 2017/0068214 | A1 * | 3/2017 | Tsai | G03H 1/0244 |
| 2017/0097558 | A1 * | 4/2017 | Belkin | G02F 1/3556 |
| 2017/0221959 | A1 | 8/2017 | Udrea et al. | |
| 2017/0234799 | A1 * | 8/2017 | Marks | G01N 33/54326 356/301 |
| 2017/0234825 | A1 * | 8/2017 | Elibol | G01N 27/3278 204/403.14 |
| 2017/0343419 | A1 * | 11/2017 | Hopper | G01J 3/0291 |
| 2018/0045953 | A1 * | 2/2018 | Fan | G02B 27/0012 |
| 2018/0059440 | A1 * | 3/2018 | Yu | G02F 1/0018 |
| 2018/0069631 | A1 * | 3/2018 | Ashrafi | H04B 10/2507 |
| 2018/0129116 | A1 * | 5/2018 | Akselrod | G02F 2/02 |
| 2018/0146512 | A1 | 5/2018 | Pindl et al. | |
| 2018/0156949 | A1 * | 6/2018 | Tsai | G02B 5/008 |
| 2018/0172510 | A1 * | 6/2018 | Rosen | G01J 3/0256 |
| 2018/0217069 | A1 * | 8/2018 | Pazos-Perez | G01N 21/658 |
| 2018/0224574 | A1 * | 8/2018 | Lee | G02B 1/002 |
| 2018/0231702 | A1 * | 8/2018 | Lin | G02B 6/0016 |
| 2018/0241131 | A1 * | 8/2018 | Akselrod | G02F 1/292 |
| 2018/0248268 | A1 * | 8/2018 | Shvets | H01Q 15/0086 |
| 2018/0341090 | A1 * | 11/2018 | Devlin | H01L 31/02 |
| 2018/0346346 | A1 * | 12/2018 | Zhu | C25D 11/045 |
| 2018/0356290 | A1 * | 12/2018 | Winger | G01J 5/061 |
| 2019/0033682 | A1 * | 1/2019 | Kafaie Shirmanesh | G02F 1/292 |
| 2019/0056544 | A1 * | 2/2019 | Bahabad | G02B 5/203 |
| 2019/0086683 | A1 * | 3/2019 | Aieta | G02B 1/002 |
| 2019/0285798 | A1 * | 9/2019 | Akselrod | G02B 6/42 |
| 2019/0323967 | A1 * | 10/2019 | Tao | G01N 21/25 |
| 2020/0021782 | A1 * | 1/2020 | Sugizaki | G02B 5/201 |

OTHER PUBLICATIONS

Fu et al., A thermal emitter with selective wavelength: Based on the coupling between photonic crystals and surface plasmon polaritons. J Applied Physics Feb. 3, 2009;105;033505, 6 pages.

Haghi et al., Wearable Devices in Medical Internet of Things: Scientific Research and Commercially Available Devices. Healthc Inform Res. Jan. 2017;23(1):4-15.althc Inform Res. Jan. 2017;23(1):4-15.althc Inform Res. Jan. 2017;23(1):4-15.

Hildenbrand et al., Micromachined Mid-Infrared Emitter for Fast Transient Temperature Operation for Optical Gas Sensing Systems. IEEE Sensors. 2008;10(2):353-362.

Ji et al., Narrow-band Midinfrared Thermal Emitter Based on Photonic Crystal for NDIR Gas Sensor. Proceedings of 2010 10th IEEE International Conference on Solid-State and Integrated Circuit Technology. Nov. 1, 2010, pp. 1459-1461.

Kady et al., Photonic crystal high-efficiency multispectral thermal emitters. Applied Physics Letters. Oct. 2008;93:153501, 3 pages.

Kim et al., Potential and Challenges for Mid-Infrared Sensors in Breath Diagnostics. IEEE Sensors Journal. Jan. 2010;10(1):145-158.

Mathew et al., Technologies for Clinical Diagnosis Using Expired Human Breath Analysis. Diagnostics (Basel). Feb. 2, 2015;5(1):27-60.

Sawada et al., Surface Plasmon Polariton Based Wavelength Selective IR Emitter Combined with Microheater. Proceedings of 2013 International Conference on Optical MEMS and Nanophotonics (OMN), IEEE. Aug. 2013 18:45-46.

Wang et al., Lambertian thermal emitter based on plasmonic enhanced absorption. Opt Express. Aug. 8, 2016;24 (16):18382-7.

(56) References Cited

OTHER PUBLICATIONS

Wang et al., Omnidirectional thermal emitter based on plasmonic nanoantenna arrays. Opt Express. Jan. 27, 2014;7;22 (2):1313-8.
InfraTec, Windows and Filter. Retrieved Jul. 18, 2010 online at: https://www.infratec-infrared.com/downloads/en/sensor-division/application-notes/infratec-application-notes-windows-and-filter.pdf. 17 pages.

* cited by examiner

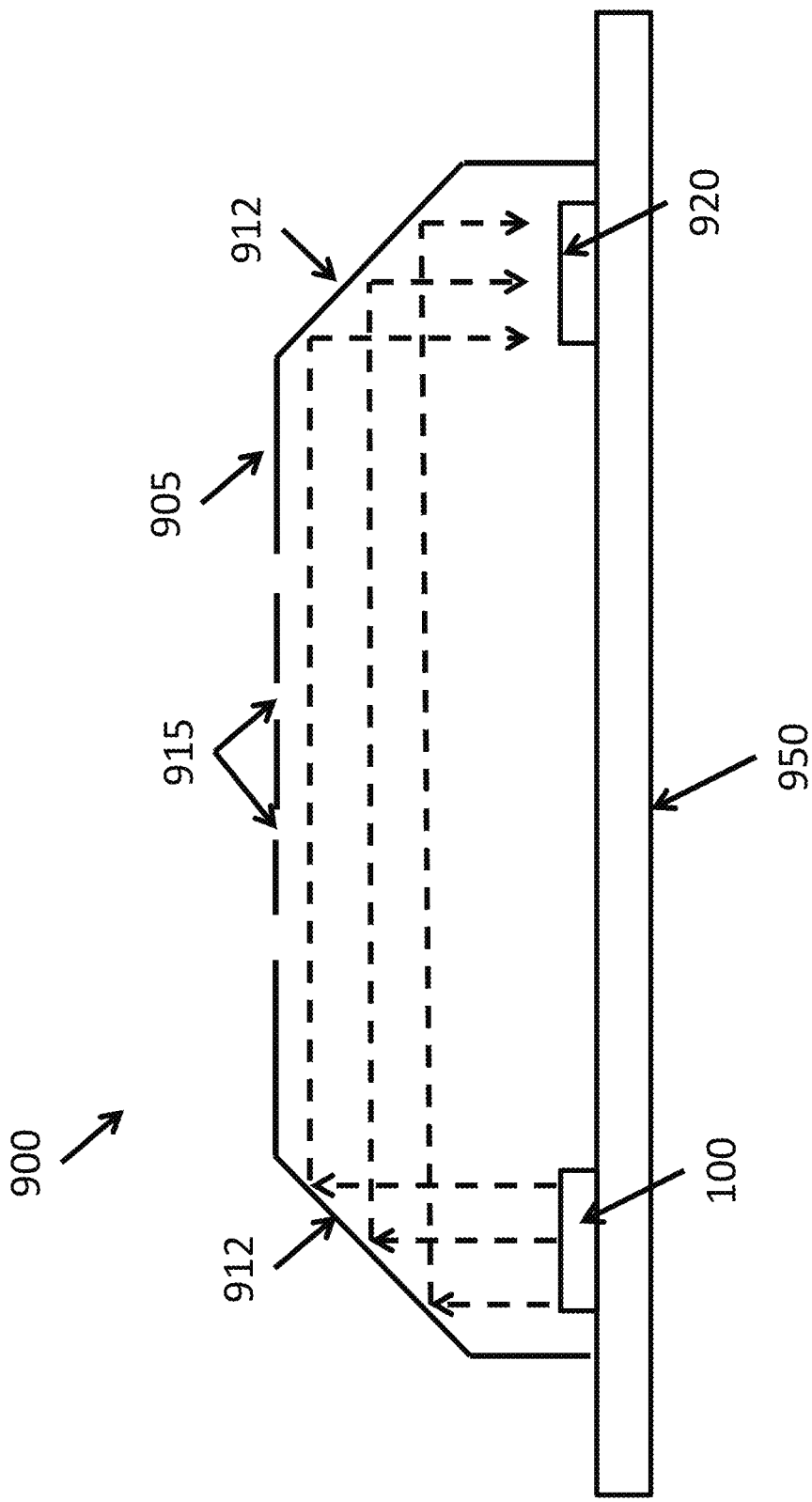

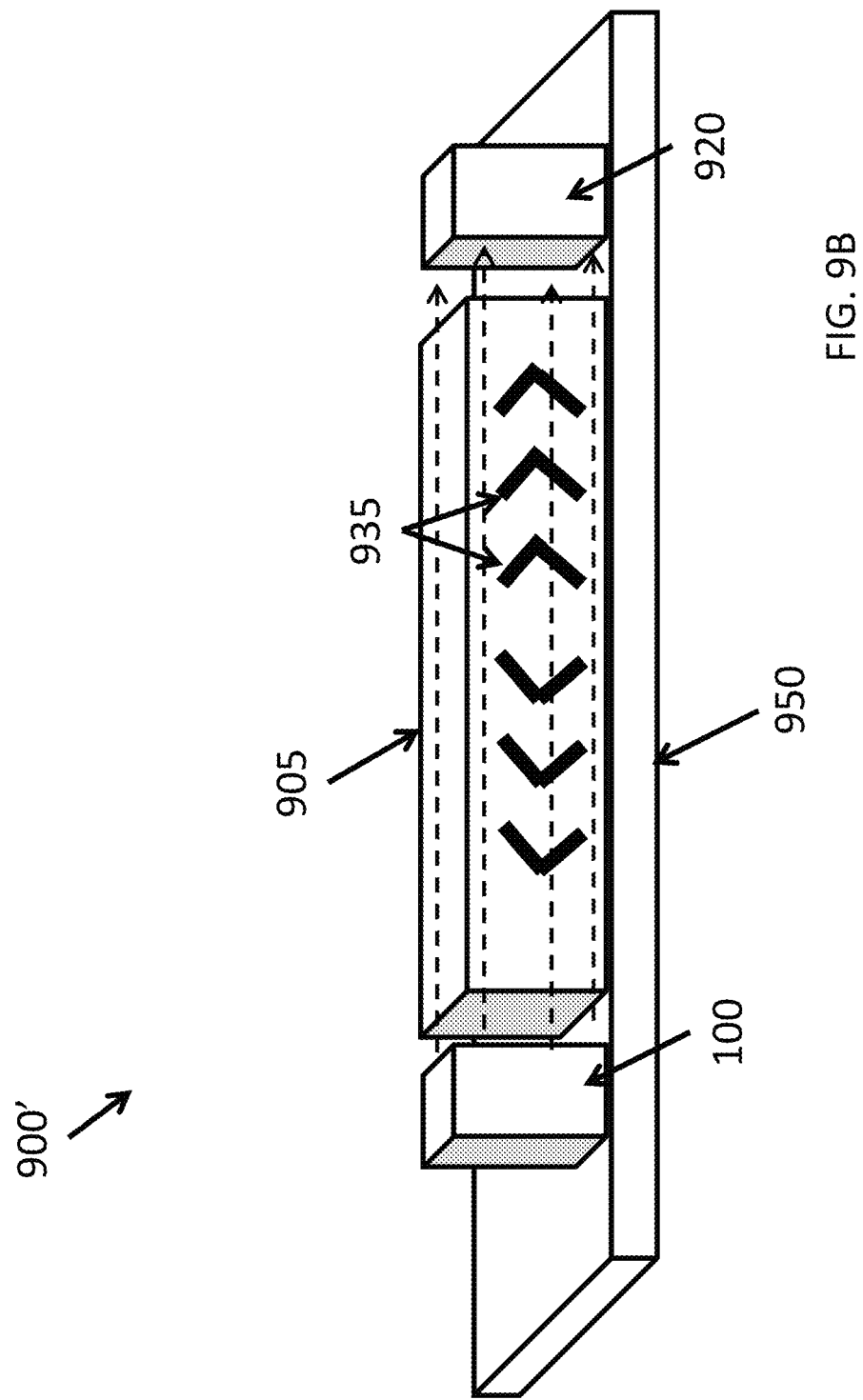

COMPACT GAS SENSORS

RELATED APPLICATIONS

This application claims priority to U.S. Provisional Application No. 62/810,120, filed Feb. 25, 2019 and also claims priority to U.S. Provisional Patent Application No. 62/672,354, filed May 16, 2018, the entire contents of the above applications being incorporated herein by reference in their entireties.

FIELD OF THE INVENTION

This invention is related to infra-red gas sensors, in particular compact and low-power-consumption gas sensors for mobile applications that employ thin film plasmonic emitters.

BACKGROUND OF THE INVENTION

Non-dispersive infrared (NDIR) gas sensors conventionally include a heating element as a source of infrared (IR) emission, a band-pass filter or filters for controlling the wavelength of emitted or detected light, a gas cell containing a gas mixture under test, and a photodetector for measuring intensity of light that passes through the gas cell. The presence or concentration of specific gas molecules in gas mixtures within the gas cell is determined by monitoring the absorption of optical radiation transmitted through the gas cell. When optical radiation from an infrared emitter is absorbed by the gas molecule at its characteristic wavelength, the measured value of optical radiation at that specific wavelength is reduced. By analyzing measured optical radiance using a photodetector (e.g., located at the end of the gas cell opposite to the emitter), the type and concentration of gas molecules in the gas cell can be determined.

In order to improve sensitivity, selectivity, and dynamic range of the NDIR gas sensor, various emitters, photodetectors, gas cell geometries, and optical trains have been designed, tested, and incorporated into gas sensor products. For example, compact NDIR gas sensors can use a cylindrical gas cell geometry which provides a highly compact gas sensor without compromising the detector sensitivity. A U-shaped folded optical waveguide configuration with increased beam path length can be used to improve sensitivity without increasing the footprint of the gas sensor. Generally, compact NDIR gas sensors with improved sensitivity can be produced by employing specially designed gas cell geometries.

Many conventional gas sensors employ broadband blackbody radiation sources as emitters. In such cases, narrow band-pass filters are used to block out-of-band radiation from reaching the photodetector. Out-of-band radiation is not absorbed by gas molecules of interest. When using a narrow band-pass filter, typically greater than 90% of the radiation from the blackbody emitter is converted into wasted heat. The heat generation results in significantly increased temperatures for the gas sensor module; consequently, a fairly sophisticated heat management scheme is required to prevent hotspots from building within the sensor module. Moreover, poor energy efficiency of the conventional blackbody emitter means that gas sensor devices with blackbody emitters require large amounts of electric power, typically greater than 100 mW in continuous operation. Further, large electric power requirements and potential hot spot generation limit the scope of applications for gas sensors with conventional blackbody emitters and make them intrinsically unsafe for use in hazardous environments.

Microfabricated thin film membrane-based IR emitters have been reported. The microfabricated thin film membrane emitter, sometimes called a "micro-hotplate," has membrane thicknesses in a range from a few micrometers to a few tens of micrometers ($\mu m$). Because of the small thermal mass of the thin film membrane emitter, rapid heating and cooling of the emitter is possible while consuming only a small amount of electric power. Because of the feasibility of rapid heating and cooling, the emitter duty cycle can be reduced significantly. For example, the duty cycle can be reduced from continuous operation (i.e., 100% duty cycle) to pulsed operation (e.g., <10% duty cycle). By pulsing the emitter, electric power requirements for NDIR gas sensors can be further reduced. A platinum heater on a suspended membrane for fast transient operation is described in J. Hildenbrand et al., "Micromachined Mid-Infrared Emitter for Fast Transient Temperature Operation for Optical Gas Sensing Systems," Proceedings of IEEE Sensors 2008 Conference, the contents of which is incorporated herein by reference. By fabricating a platinum thin strip heater on top of a 15-$\mu m$-thick silicon suspended membrane, a heater modulation frequency of 10 Hz was achieved. By modulating the optical emission at the source, advanced signal processing schemes, such as signal averaging and noise reduction, can be accomplished without requiring the use of a mechanical chopper.

While thin film membrane-based emitters enable fast transient temperature operation and higher operation temperatures at reduced electric power, these emitters generate omnidirectional broadband emission. As a result, conventional NDIR gas detectors need to incorporate focusing and collimating optics to make more efficient use of the emitted radiation and narrow bandpass filters to filter out background (e.g., out-of-band) emissions. Such precision optical components increase manufacturing costs and make the resulting NDIR gas sensors fragile. In particular, additional design features are needed to make these devices mechanically robust and stable with the related downside of greater assembly and manufacturing costs.

The peak wavelength of the emitted light can be tuned to specific wavelengths by applying plasmonic emitting structures on the emitter surface. A micromachined tuned-band infrared emitter can be used in which the wavelength of the emitted light is controlled by fabricating a photonic band gap structure on the emitter surface. This thin membrane device can also function as a broadband infrared photodetector. However, conventional systems utilize collimating and reflecting optics, which require precision manufacturing and assembly procedures. In addition, existing systems do not describe and may be inappropriate for use with other gas sensor functionalities such as sensor signal enhancement, fine tuning of the photonic band gap structure for improved selectivity, and discrimination or elimination of environmental effects.

SUMMARY

The present invention relates to devices and methods for gas sensing with a time modulated light emitter operating at a plurality of emission wavelengths in which a reference wavelength is built-in for internal calibration. In some embodiments, the calibration can be performed continuously. Preferred embodiments employ a thin film light emitter that has a small thermal mass characterized by a narrow-bandwidth, selective emission spectrum.

Preferred embodiments can include a tunable absorption-emission band in a wavelength selective infrared emitter device. By controlling the plasmonic resonance structure of the infrared emitter, multiple narrow band emissions can be tuned and produced. The sensor provides for calibration of sensor data wherein the emitter generates a reference wavelength that is used to generate reference data that is processed in combination with the detected wavelengths from the sample to provide calibrated sensor data.

Thin film micro-hotplate IR emitters with plasmonic structures are used to produce narrow wavelength emission in some embodiments. In order to improve mechanical durability of the thin and floating membrane and heater structures, heater layers are embedded into dielectric membranes.

Preferred embodiments can include methods of detecting one or more different molecules in a gas being measured. The emission peaks of the emitter are selected to correlate with the absorption characteristics of the medium being measured.

The emitter and detector can be connected to a control circuit to control emission and detector operating parameters. The light source can comprise one or more emitters or emitter patterns to form an array, each having a different spectral distribution so that the control circuit can select different emission patterns. A temporally modulated power signal is used to adjust emitter parameters. The energy efficiency of prior devices is typically less than 10% with signal to noise ratios (S/N) of 5-10. In various embodiments described herein, systems and methods can achieve electric pulsed power efficiencies above 10% and S/N above 10, in a range from 10-20, or above 20.

BRIEF DESCRIPTION OF THE DRAWINGS

FIG. 9a is a cross-sectional schematic view of an on-board gas sensor according to various embodiments of the present invention.

FIG. 9b is a schematic view of a compact gas sensor according to various embodiments of the present invention.

DESCRIPTION OF THE INVENTION

Systems and methods described herein provide compact gas sensors with low power consumption. The gas sensors are self-calibrating and are capable of quickly and accurately detecting multiple gas spaces. The gas sensors are intrinsically safe for hazardous and explosive environmental applications.

As described herein, a low power budget NDIR gas sensor includes a thin film light source that can produce a time-modulated parallel light beam at multiple selected wavelengths. The parallel light beam from the light source passes through a gas chamber without requiring focusing or collimating optical components. In addition, the NDIR gas sensor of the current invention has a built-in referencing function. Therefore, the gas sensor is continuously self-calibrated against environmental changes (e.g., changes in temperature or relative humidity) and aging without needing separate environmental sensor components and compensation electrical circuits. Due to an extremely small thermal mass and non-blackbody emission of the thin film emitter, gas sensors described herein are intrinsically safe which is of great benefit for use in hazardous environments. NDIR gas sensors described herein are extremely compact and consume low amounts of power, and they are easy to integrate into existing mobile device platforms.

Compact and low power gas sensors can be useful in a variety of lightweight and mobile applications. For example, compact gas sensors can be used for point-of-care health monitoring such as breath diagnosis, portable environmental gas monitoring devices, especially for hazardous environment applications, and embedded smart sensors for wearable medical devices and internet-of-things (IOT) applications. In addition, highly efficient and narrow bandwidth emitting thin plasmonic emitters can find application in medical diagnosis devices that require narrow bandwidth mid-IR light sources.

Figure 1:
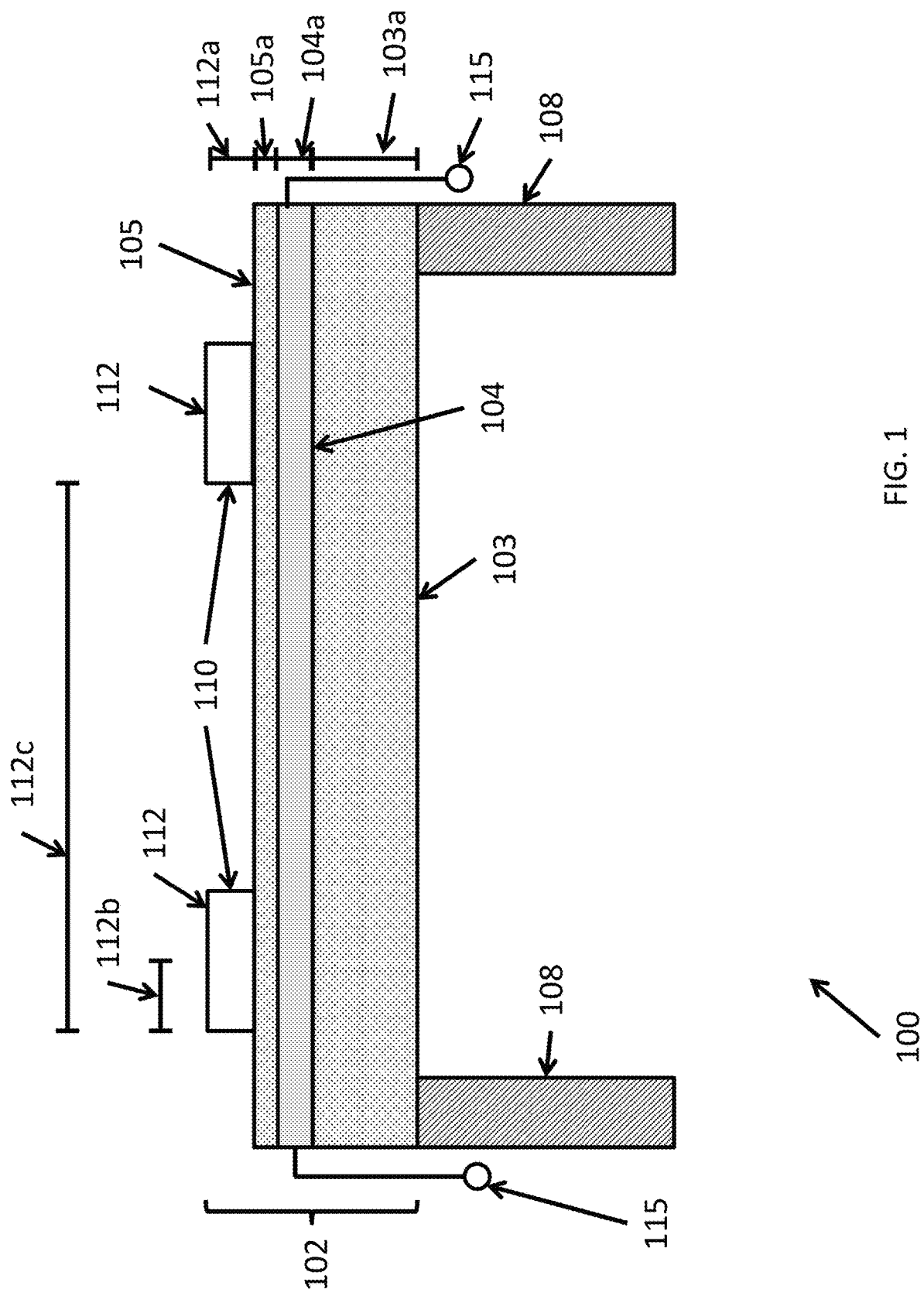
FIG. 1 is a cross-sectional view of a thin film plasmonic emitter according to various embodiments of the present invention.

FIG. 1 shows a schematic cross section of a thin film plasmonic IR emitter 100 according to various embodiments of the present invention. The emitter 100 includes a membrane layer 102 and a support layer 108. The membrane layer 102 includes a base layer 103, a continuous conductive layer 104, a dielectric layer 105, and a patterned conductive layer 110. When activated, the thin film plasmonic IR emitter 100 can produce and emit narrow bandwidth emission peaks of infrared radiation.

The support layer 108 can be used as a structural support during microfabrication and packaging of the thin film membrane plasmonic emitter 100. In some embodiments, the support layer 108 comprises silicon. In some embodiments, the support layer 108 can have a thickness in a range from 50 μm to 2,000 μm or more preferably in a range from 300 μm to 700 μm. One of ordinary skill in the art will appreciate that thicker or thinner structural support provided by the support layer 108 may be used depending upon microfabrication process design and gas sensor product performance requirements.

In various embodiments, the membrane layer 102 can have a thickness of less than 8 μm, less than 5 μm, or less than 1 μm. A thinner membrane layer 102 leads to more rapid heating and cooling and can enable a high modulation rate. However, the membrane layer 102 is still thick enough to be self-supporting and to be highly reproducible based upon the manufacturing technologies and process used to fabricate the layer. In some embodiments, the membrane layer 102 can have a thickness greater than 0.2 μm. The membrane layer 102 includes the patterned conductive layer 110 having a plurality of relief features provided in a periodic spatial configuration, the dielectric layer 105 underlying the patterned conductive layer 110, the continuous conductive layer 104 underlying the dielectric layer 105, and the base layer 103 underlying the continuous conductive layer 104. The membrane layer 102 can act as a structural support of the completed thin film membrane emitter 100 in some embodiments. In some embodiments, at least a portion of the membrane layer 102 is not in contact with the support layer 108. For example, the membrane layer 102 can be suspended over a recessed or removed portion of the support layer 108. The recess or gap in the support layer 108 can be created using wet etching, dry etching, laser ablation, or any other suitable technique to remove material. In some embodiments, freeing the portion of the membrane layer 102 by removing contact with the support layer 108 enables the portion of the membrane layer 102 to change conformation (e.g., expand, contort, bend, or fold) when heated to alleviate stress forces on the membrane layer 102. In some embodiments, the membrane layer 102 can have an active area. The active area of the membrane layer is the top surface area from which light is emitted.

The base layer 103 can comprise a dielectric material or other electrically insulating material in some embodiments. In some embodiments, the base layer 103 can include alumina ($Al_2O_3$), silicon dioxide ($SiO_2$), or silicon nitride ($Si_3O_4$). In a preferred embodiment, the base layer 103 can include alumina because of its favorable coefficient of thermal expansion. In various embodiments, the base layer 103 can remain stable at high temperatures. In a preferred embodiment, the base layer 103 is produced using semiconductor processing and/or microfabrication processing tools. The base layer 103 can have a thickness 103a in a range from 0.1 μm to 3 μm in some embodiments. The thickness 103a of the base layer 103 can be chosen based upon requirements for manufacturing reproducibility. The base layer 103 can function as a high temperature diffusion barrier, and the lower limit on thickness can be chosen to maintain this functionality in some embodiments. The upper limit on thickness can be chosen by thermal mass requirements.

The continuous conductive layer 104 can include a conducting material in some embodiments. For example, the continuous conductive layer 104 can include a semiconductor or metal material. The continuous conductive layer 104 can have a thickness 104a in a range from 0.05 μm to 3 μm in some embodiments. The thickness 104a can be selected by balancing heating capacity and manufacturing reproducibility with the desired heater electrical current or power and considerations regarding thermal mass of the layer. In some embodiments, the continuous conductive layer 104 is deposited onto the base layer 103 using chemical or physical vapor deposition or epitaxial techniques. In some embodiments, the continuous conductive layer 104 can be created by depositing material into an existing wafer. In some embodiments, the continuous conductive layer 104 can be coupled to one or more electrical contacts 115. The electrical contacts 115 can provide power to the thin film plasmonic IR emitter 100. The continuous conductive layer 104 can include metals in some embodiments. In exemplary embodiments, the continuous conductive layer 104 can include metals with high temperature stability such as platinum, molybdenum, tungsten, titanium, tantalum or alloys of these metals with either other or other materials. In some embodiments, the continuous conductive layer 104 can include a highly doped semi-metallic semiconducting material such as polycrystalline silicon.

The dielectric layer 105 can include a dielectric material or other electrically insulating material in some embodiments. The dielectric layer 105 can have a thickness 105a in a range from 0.05 μm to 1 μm in some embodiments. In some embodiments, the dielectric layer 105 is deposited onto the continuous conductive layer 104 using chemical or physical vapor deposition or other dielectric film deposition techniques. In some embodiments, the dielectric layer 105 can include materials that are stable and insulating at high temperature. In some embodiments, the dielectric layer 105 can include materials that are transparent to infrared radiation. The dielectric layer 105 can include alumina or rare-earth oxides (e.g., yttria or hafnia) in some embodiments.

The patterned conductive layer 110 can include a plasmonic structure in some embodiments. The patterned conductive layer 110 can include a plurality of relief features or structures 112. The relief features 112 can have a thickness 112a and a lateral dimension 112b. The lateral dimension 112b can include a length, width, diameter, or radius in various embodiments. In some embodiments, the relief features 112 can be separated from one another by adjacent recessed areas. In some embodiments, the relief features 112 can be separated from one another at a pitch 112c. The pitch 112c can be the same in all directions or can differ along different directions or axes. By patterning relief features 112 into a periodic structure, the main surface plasmon polariton (SPP) modes of the interface between the patterned conductive layer 110, dielectric layer 105, and continuous conducting layer 104 are established in the plasmonic emitter structure. The SPPs are coupled modes of light and surface plasma waves and are responsible for narrow band emission/absorption of light from the plasmonic emitter surface. In some embodiments, the pattern of relief features 112 can include defects (i.e., disruptions to the periodicity of the features). In some embodiments, the pattern of relief features 112 can include supercell structures as described in greater detail below with respect to FIGS. 14 and 15.

The relief features 112 can be formed through addition (e.g., deposition) or removal (e.g., etching) of material. Each relief features 112 can be symmetric or asymmetric. In some embodiments, the relief features 112 can include a single material or multiple materials. For example, the relief features 112 can include a first material coated or covered by a second material. The relief features 112 can include a variety of cross-sectional shapes including, but not limited to, circles, squares, triangles, rectangles, pentagons, hexagons, or other polygons. The cross-sectional shape of the relief features 112 can be irregular. The relief features can include divots formed in the material in some embodiments. The relief structures 112 can have a thickness 112a in a range from 0.05 µm to 5 µm in some embodiments.

The relief features 112 in the patterned conductive layer 110 can have properties (e.g., width, height, or inter-feature spacing) designed to cause emission of radiation at particular wavelengths. In some embodiments, properties of the relief features 112 can be chosen to create peak emission at the absorption wavelength of a target gas molecule. For example, properties of the features can be chosen to match the peak absorption wavelength for ammonia (3.03 µm), methane (3.30 µm), acetone (3.33 µm), formaldehyde (3.6 µm), carbon dioxide (4.26 µm), and/or carbon monoxide (4.70 µm). In some embodiments, properties of the relief features 112 can be determined through computer simulation and modeling of the electromagnetic properties of the emitter 100.

Figure 2:
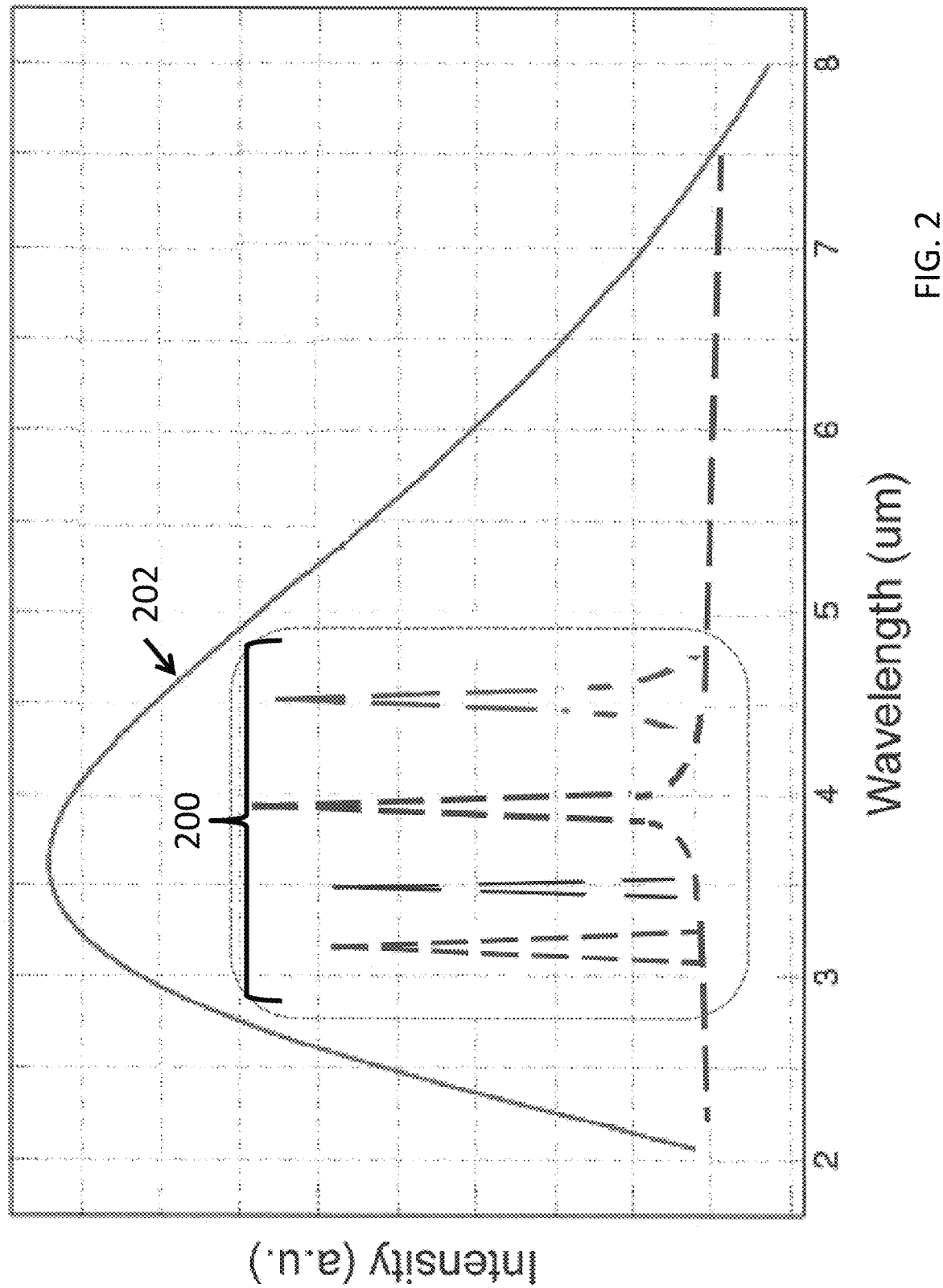
FIG. 2 is a comparative graphical representation of IR emission spectra of a conventional blackbody emitter and the thin film plasmonic emitter according to various embodiments of the present invention.

When heating the plasmonic IR emitter to high temperatures, e.g., 700° C., one or more narrow bandwidth emission peaks 200 are emitted at various peak positions as graphically illustrated in FIG. 2. A broadband blackbody emission 202 at 700° C. is shown as a comparison.

NDIR gas sensors can be calibrated against signal drift induced by the environment or aging of components. Conventional NDIR gas sensors use a reference peak and/or a gas cell to compensate environmental signal drifts by employing a narrow band pass filter at a non-absorbing wavelength (e.g. 3.90 µm peak position) and a second photodetector placed upon a different optical path. As such, conventional systems require additional components at different positions relative to the gas cell. As a result, conventional gas sensors are bulkier and more complex than necessary and have poor calibration accuracy. For example, environment-induced sensor signal drifts, such as temperature and relative humidity (RH) effects, and aging, can't be accurately compensated and calibrated because each component along the separate optical paths can have different environmental drift and aging characteristics.

In accordance with various embodiments, the emitter 100 can be self-calibrated against environmental and age-related drift. In an exemplary embodiment, a reference peak is identified at a wavelength at which no common gas molecule in ambient air has strong absorption. In the mid-IR range (between 3-5 µm), an exemplary narrow band reference peak can be centered at 3.90 µm. The reference peak can be at a higher or lower wavelength than related characteristic absorption peaks for specific gas molecules or may be between characteristic absorption peaks. While sensing any specific gas molecule, the emitter 100 can simultaneously be calibrated in situ (i.e., in real time) against environmental effects or drifts. Environmental effects include temperature drifts of all electronic components or photodetectors, normal aging of components, and relative humidity (RH) effects.

Figure 3:
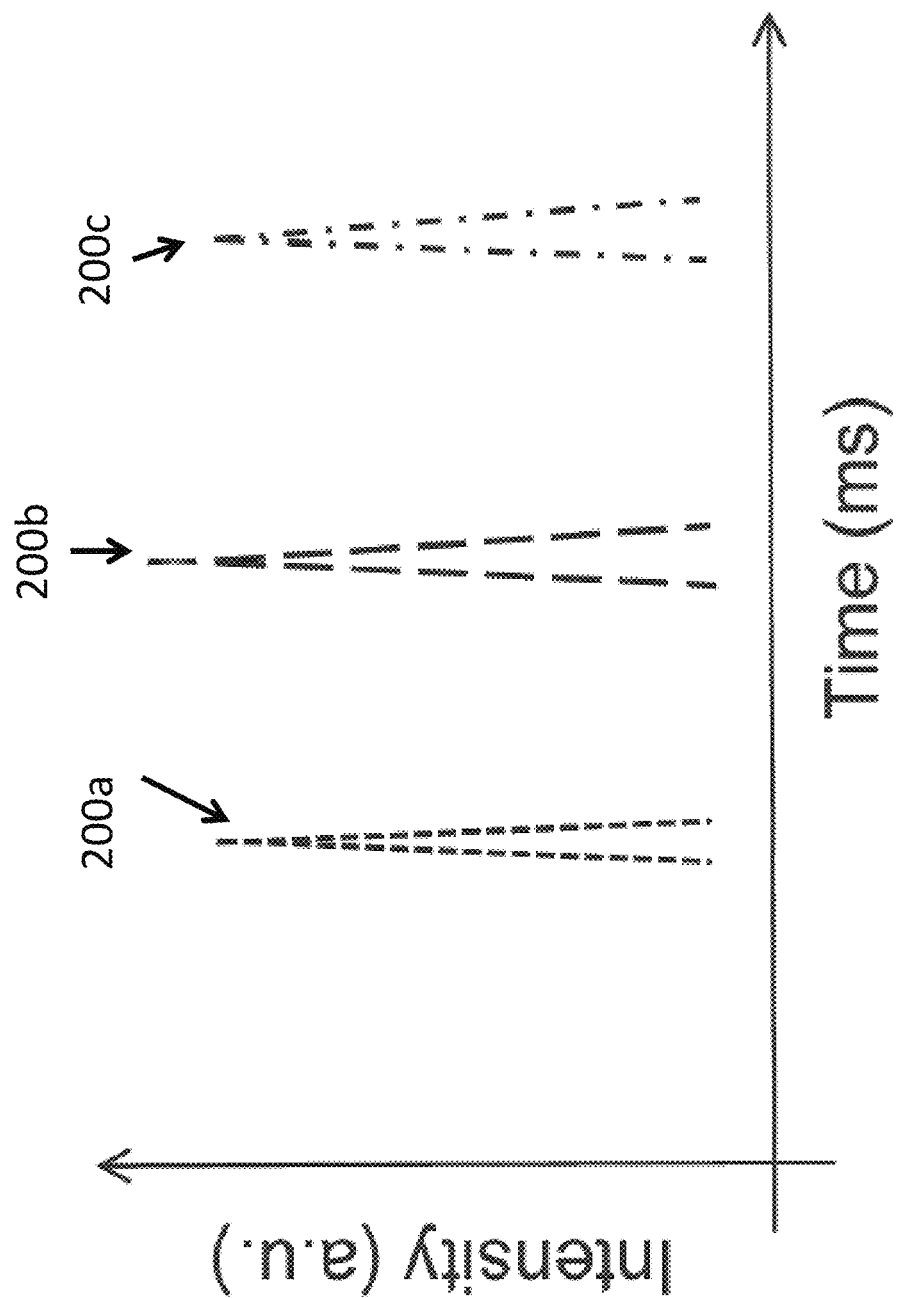
FIG. 3 is a graphical representation of time-modulated IR emission spectra of the thin film plasmonic emitter according to various embodiments of the present invention.

In-situ calibration against environmental effects of emitters 100 according to the present disclosure is illustrated in FIG. 3. Time-modulated narrow bandwidth emission peaks can be emitted by the emitter 100 with a separation between peaks on the order of a few milliseconds upon heating from low temperatures. Because of the extremely small thermal mass of the membrane layer 102, rapid heating and cooling with controlled heating/cooling rates of the emitter 100 are possible. In some embodiments, the membrane layer 102 has a mass of about 70 µg with a 3 mm diameter active area. Upon heating, the first peak 200a appears at a low temperature. As emitter temperature increases, a second peak 200b and a third peak 200c appear a few milliseconds after. Upon cooling down from high temperatures, the third peak 200c, second peak 200b, and first peak 200a reappear consecutively. In some embodiments, measurements can be made using all peaks both as temperature increases and as temperature decreases. By heating and cooling, multiple measurements for each wavelength can be obtained in a single sweep. In some embodiments, the emitter 100 can be heated to maximum temperatures, e.g., ~700° C., and cooled to ambient temperatures in about 10 milliseconds. In some embodiments, sensor signals measured during heating and cooling cycles can be averaged to increase the sensitivity of the gas sensor.

In some embodiments, the narrow band emission peaks can be specially designed to match the characteristic wavelength of specific gas molecules. For example, the first peak 200a can be used for carbon monoxide (CO) detection, the second peak 200b can be used as the reference peak, and the third peak 200c can be used for methane ($CH_4$) detection. The characteristic emission peaks can be used to sense and measure the associated gas molecules. In some embodiments of the present system measurement and calibration can be performed using the same system and components over a time span of less than 10 milliseconds. As a result, measured gas sensor data can be well calibrated and accurate.

Figure 4:
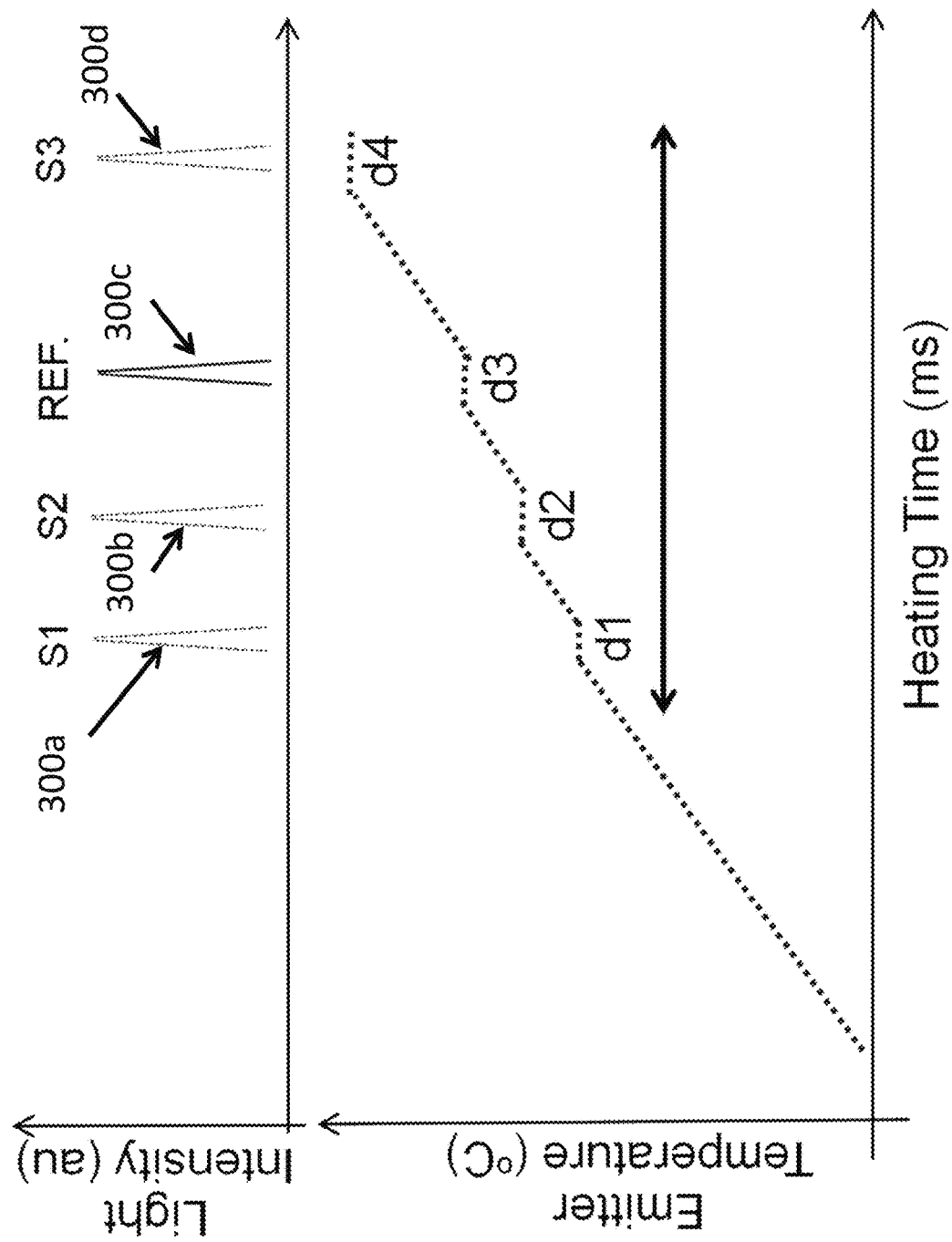
FIG. 4 illustrates the emitted light spectrum and emitter temperature for the emitter as a function of time during a heating cycle according to various embodiments described herein.

The thermal mass of the thin plasmonic emitter 100 can be defined as $C_{th}=m_e*C_p$ where $m_e$ is the mass of the active membrane. For a membrane mass of 68.7 micro-grams and an active membrane area of 0.071 $cm^2$ corresponding to a 3-mm-diameter emitter, the thermal mass is $1.92\times10^{-5}$ J/K. In some embodiments, the emitter 100 can be heated to a temperature of 700° C. in less than 50 msec to emit narrow band emission radiation for NDIR gas sensing. As shown in FIG. 4, the emitter 100 emits multiple narrow band peaks 300a, 300b, 300d, which match the absorption characteristic peaks of certain target gas molecules, upon heating of the emitter 100. The reference peak 300c is also emitted for purposes of gas sensor calibration. By using measured light intensity at the characteristic peak position, the presence and concentration of target gas molecules can be calculated in certain embodiments by using a pre-established lookup table.

The gas sensing operation can be performed during cooling of the emitter 100. Considering the extremely small thermal mass of the emitter 100 in some embodiments, there may be no significant hysteresis in temperature during heating and cooling. By averaging sensor signals from heating and cooling cycles, sensor sensitivity can be improved. In some embodiments, the emitter 100 can be controlled to dwell at certain temperatures. For example, it may be desirable to sustain emission at a particular wavelength to accommodate certain sensor signal processing schemes and/or photodetector response times. In some embodiments, the emitter 100 can be controlled to dwell for up to a few milliseconds of dwell time, as indicated by labels d1, d2, d3, and d4 in FIG. 4, to enable completion of signal processing at each sensing point. If a fast test cycle is required, the emitter 100 can be controlled to cool down only to intermediate temperatures, e.g., ~300° C., following by heating back to high temperatures, e.g., 600° C. Such fast temperature cycling is illustrated by the bold arrow line in FIG. 4.

Theoretically, there is no limitation as to how far the wavelength can be swept within the mid-infrared range (3-5 μm). In some embodiments, a temperature of ~300° C. can correspond to an output of light at 5 μm peak wavelength while a temperature of ~700° C. can correspond to an output of light at 3 μm peak wavelength. In some embodiments, the output wavelength can be made longer (limited only by ambient temperatures, e.g., about 50° C.) and can be made shorter (at high temperatures, e.g., 2 μm peak output at ~1175° C.).

Because of the low thermal mass of the membrane layer 102, the light emission can be effectively modulated by quickly heating and cooling the emitter 100. The resulting time-modulated light emission can improve sensitivity by enabling the possibility of signal averaging. In conventional systems, extra components are needed to achieve the same effect such as choppers or lock-in amplifiers. In some embodiments, the emitter 100 can be coupled to a demodulation circuit that demodulates light signals detected by a photodetector.

In some embodiments, the sensor signal is in-situ calibrated using the same test loop and components as measurement signals by using the reference peak signal during gas sensing. As a result, sensor signal drifts due to environmental changes can be very accurately compensated. Further, in-situ (i.e., real-time) signal calibration reduces total acquisition time and electrical power required for sensor calibration and signal processing. In addition, extra sensor calibration loop and components are not required. Therefore, gas sensors using emitters 100 of the present disclosure can be designed and manufactured to be extremely compact at a low manufacturing cost. The in-situ sensor calibration procedure is illustrated in Table 1. In Table 1, M represents measurement values during heating and cooling cycles at different peak positions (M1h, M2h, M3h, M1c, M2c, M3c, etc.). In some embodiments, multiple temperature cycles (sweeps) can be used for a given sampling cycle to obtain one data (gas concentration) point. For example, a time-modulated signal averaging operation can be performed in some embodiments.

TABLE 1

An exemplary sensor signal calibration process using the in-situ reference peak according to embodiments of the present invention

| Peak Position | M1 | M2 | M2-Calibrated | M3 | M3-Calibrated | M4 | M4-Calibrated |
|---|---|---|---|---|---|---|---|
| S1 | S1-1 | S1-2 | $S1\text{-}2 \times \frac{REF2}{REF1}$ | S1-3 | $S1\text{-}3 \times \frac{REF3}{REF1}$ | S1-4 | $S1\text{-}4 \times \frac{REF4}{REF1}$ |
| S2 | S2-1 | S2-2 | $S2\text{-}2 \times \frac{REF2}{REF1}$ | S2-3 | $S2\text{-}3 \times \frac{REF3}{REF1}$ | S2-4 | $S2\text{-}4 \times \frac{REF4}{REF1}$ |
| REF | REF1 | REF2 | $\frac{REF2}{REF1}$ | REF3 | $\frac{REF3}{REF1}$ | REF4 | $\frac{REF4}{REF1}$ |
| S3 | S3-1 | S3-2 | $S3\text{-}2 \times \frac{REF2}{REF1}$ | S3-3 | $S3\text{-}3 \times \frac{REF3}{REF1}$ | S3-4 | $S3\text{-}3 \times \frac{REF4}{REF1}$ |

Figure 5A:
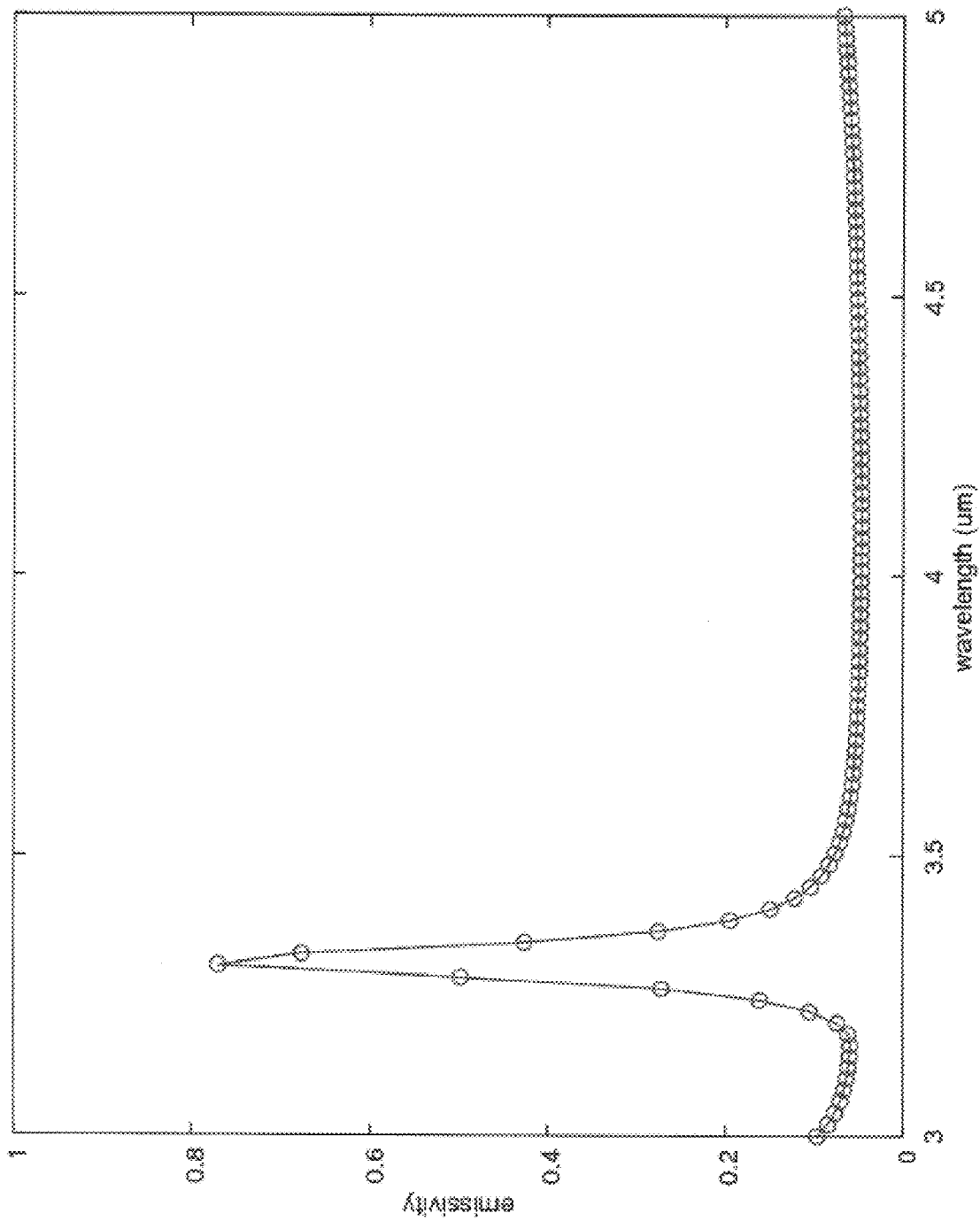
FIG. 5a is a simulated emission peak, centered at 3.3 μm, of the thin film plasmonic emitter according to various embodiments of the present invention.
Figure 5B:
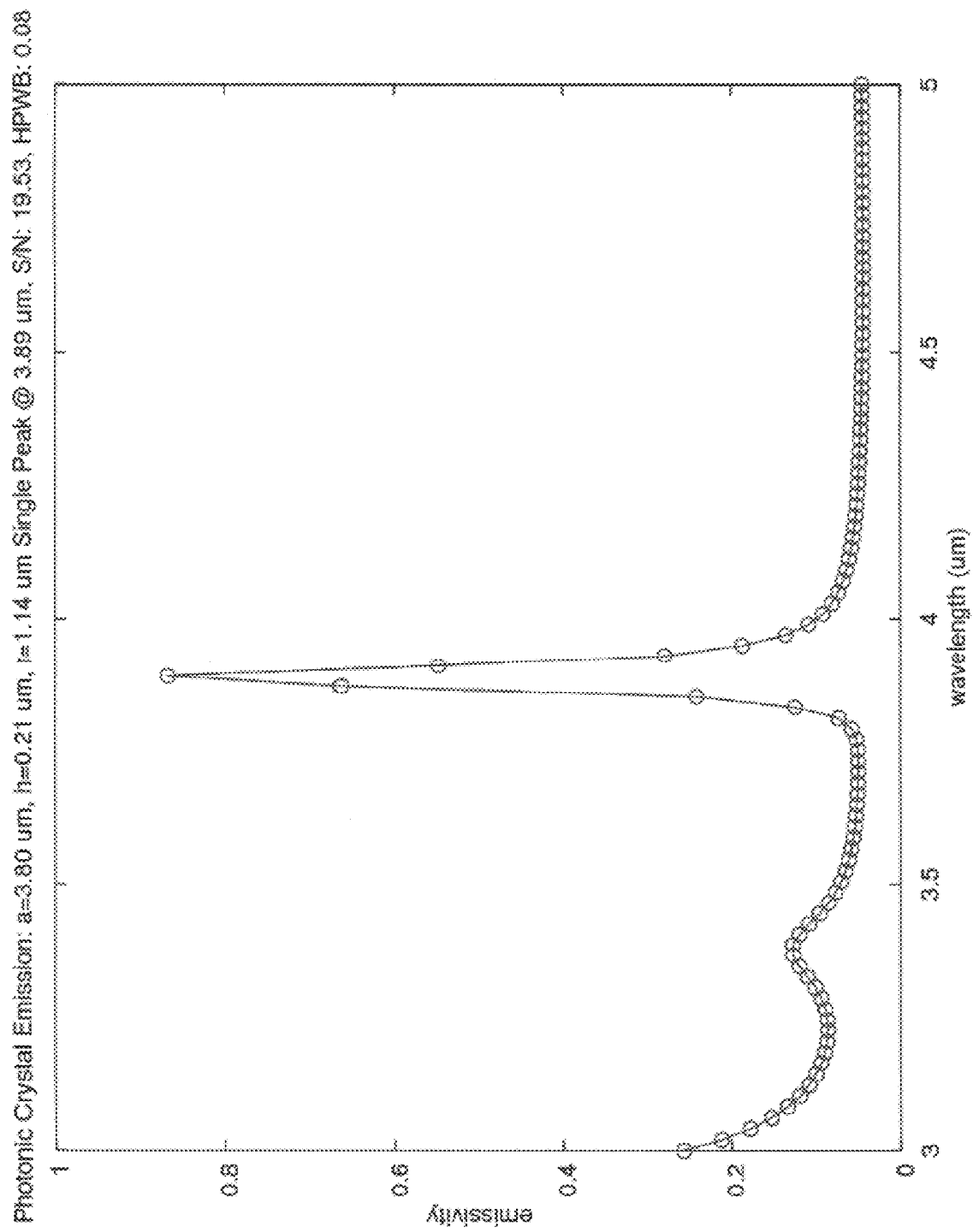
FIG. 5b is a simulated emission peak, centered at 3.89 μm, of the thin film plasmonic emitter according to various embodiments of the present invention.

FIGS. 5a and 5b are simulated emission peaks for the plasmonic emitter 100 as described herein located at 3.30 μm and 3.89 μm, respectively. In accordance with various embodiments of this description, radiation emitted from the emitter 100 can be simulated using software. The spectra of FIGS. 5a and 5b were simulated using the MIT Electromagnetic Equation Propagation (MEEP) software package. Electromagnetic simulation can be used to design plasmonic pattern structures in the patterned conductive layer 110 on the surface of the emitter 100 to produce desirable IR emission peaks. The properties of the target emission peaks and simulation constraints used for this simulation are summarized in Table 2. Desirable emission peak properties, such as peak position (wavelength) and half power beam width (HPBW), can be determined while considering functional performance, such as producing the reference peak and the desired sensing peak or peaks, of the resulting gas sensor. In some embodiments, the simulation constraints on the plasmonic structure can be determined by considering microfabrication procedures, and consequently, the cost of manufacturing the thin plasmonic emitter 100.

TABLE 2

Specifications for simulation of plasmonic structures

| Property | Specification | Note |
|---|---|---|
| Emission Peaks Position (μm) | 3.30, 3.90, 4.26, and 4.66 | Single or multiple targets |
| HPBW (nm) | <150 | Fixed target |
| S/N ($I_{peak}/I_{background}$) | >10 | Fixed target |
| Simulation Parameters | | |
| Resistivity of metal, patterned and continuous conductive layers (μΩ-cm) | 10 | 5-100 constraints |
| Thickness 105a (μm) | 0.1 | 0.02-0.2 constraints |
| Thickness 112a (μm) | 0.15 | 0.05-0.2 constraints |
| Thickness 104a (μm) | 0.15 | 0.05-0.2 constraints |

TABLE 2-continued

Specifications for simulation of plasmonic structures

| | Specification | Note |
|---|---|---|
| Thickness 103a (μm) | 0.4 | 0.2-2 constraints |
| Resistivity of dielectric layer and base layer (Ω-cm) | >1 × 10$^6$ | No constraints |
| Pitch 112c (μm) | >1 | No constraints |
| Radius 112b (μm) | >0.3 | No constraints |

As shown in FIG. 5a, an emission peak having a fairly narrow bandwidth, HPBW, of 120 nm and a center position at 3.30 μm can be produced by fabricating the patterned conductive layer 110 with circular relief structures 112 each having a 0.96 μm radius 112b and 210 nm thickness 112a. The pitch 112c of the relief structures 112 is 3.2 μm. Shown in FIG. 4b, a very narrow bandwidth emission peak can be produced (HPBW of 80 nm, center position at 3.90 μm) by fabricating the patterned conductive layer 110 with circular relief structures 112 each having a 1.14 μm radius 112b and 210 nm thickness 112a. The relief structures 112 are fabricated at a pitch 112c of 3.8 μm. As demonstrated in FIGS. 5a and 5b, very narrow emission peaks can be produced at both reference and sensing wavelengths using the same relief structure thickness 112a while varying pitch 112c and radius 112b of the relief structures 112 in the patterned conductive layer 110.

Figure 6:
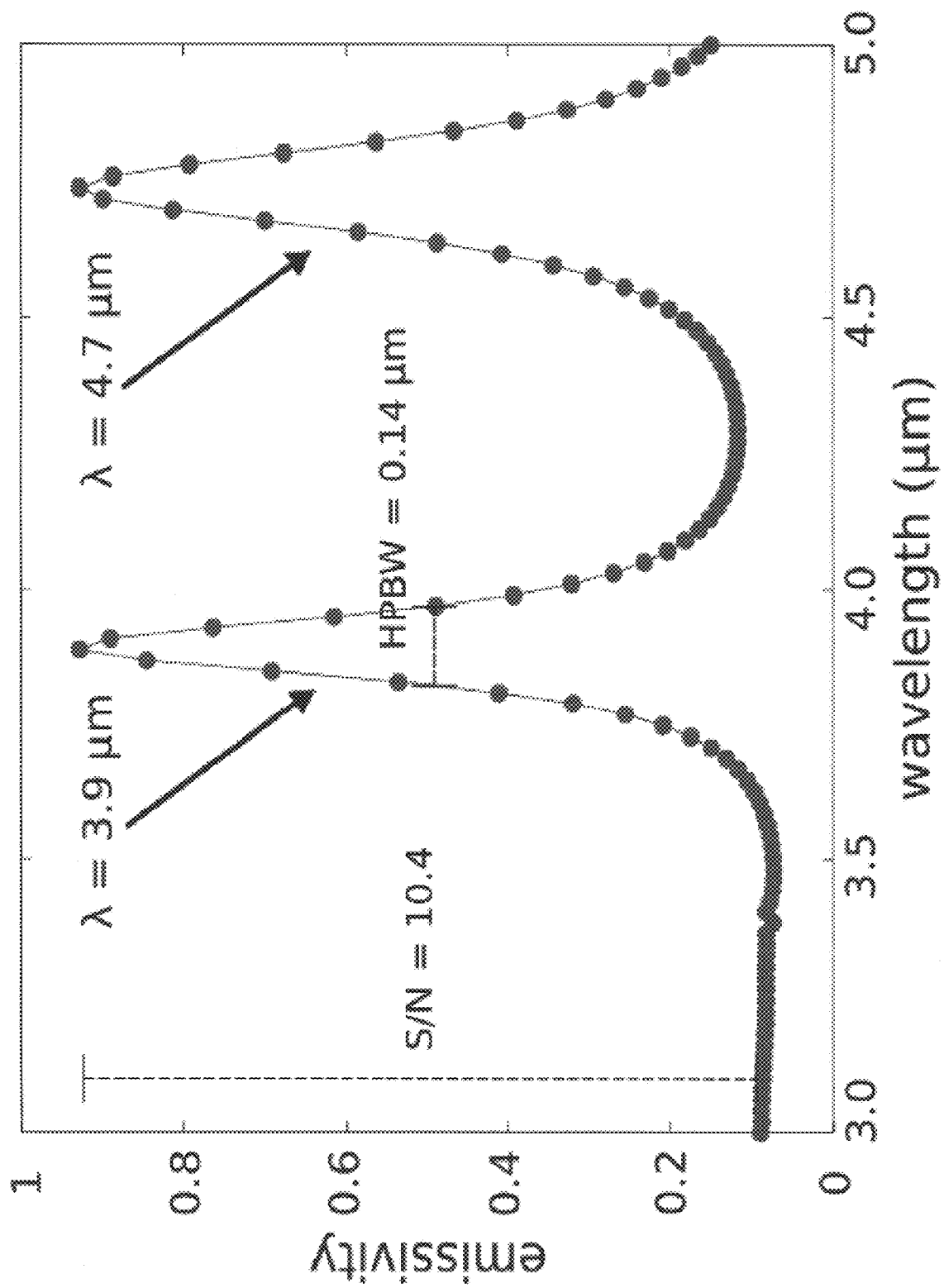
FIG. 6 is simulated dual emission peaks, centered at 3.90 μm and 4.70 μm, of the thin film plasmonic emitter according to various embodiments of the present invention.

In some embodiments, multiple emission peaks can be created using relief structures 112 having the same feature dimension and thickness across the entire emitter 100. FIG. 6 shows the reference peak at 3.90 μm and the sensing peak at 4.70 μm for an emitter according to embodiments provided herein wherein the relief structures 112 have the same layer thicknesses 112a and the same dimensions 112b. This is a significant result because a high performance plasmonic emitter 100 can thus be produced using a single cell photomask pattern. Consequently, the manufacturing cost of the thin plasmonic emitter can be reduced. The emitter 100 of the present invention can generate multiple (at least dual) emission peaks using one plasmonic emitter structure leading to simpler mask design and microfabrication processes. The light emission characteristics such as peak position, HPBW, and other characteristics of the plasmonic structure are determined by the near-field interference effects of the surface plasmon polaritons. Further, this result also suggests that multi-gas sensing is feasible using a single plasmonic emitter structure, especially with the time-modulated emitter operation and signal processing as described herein.

Figure 7:
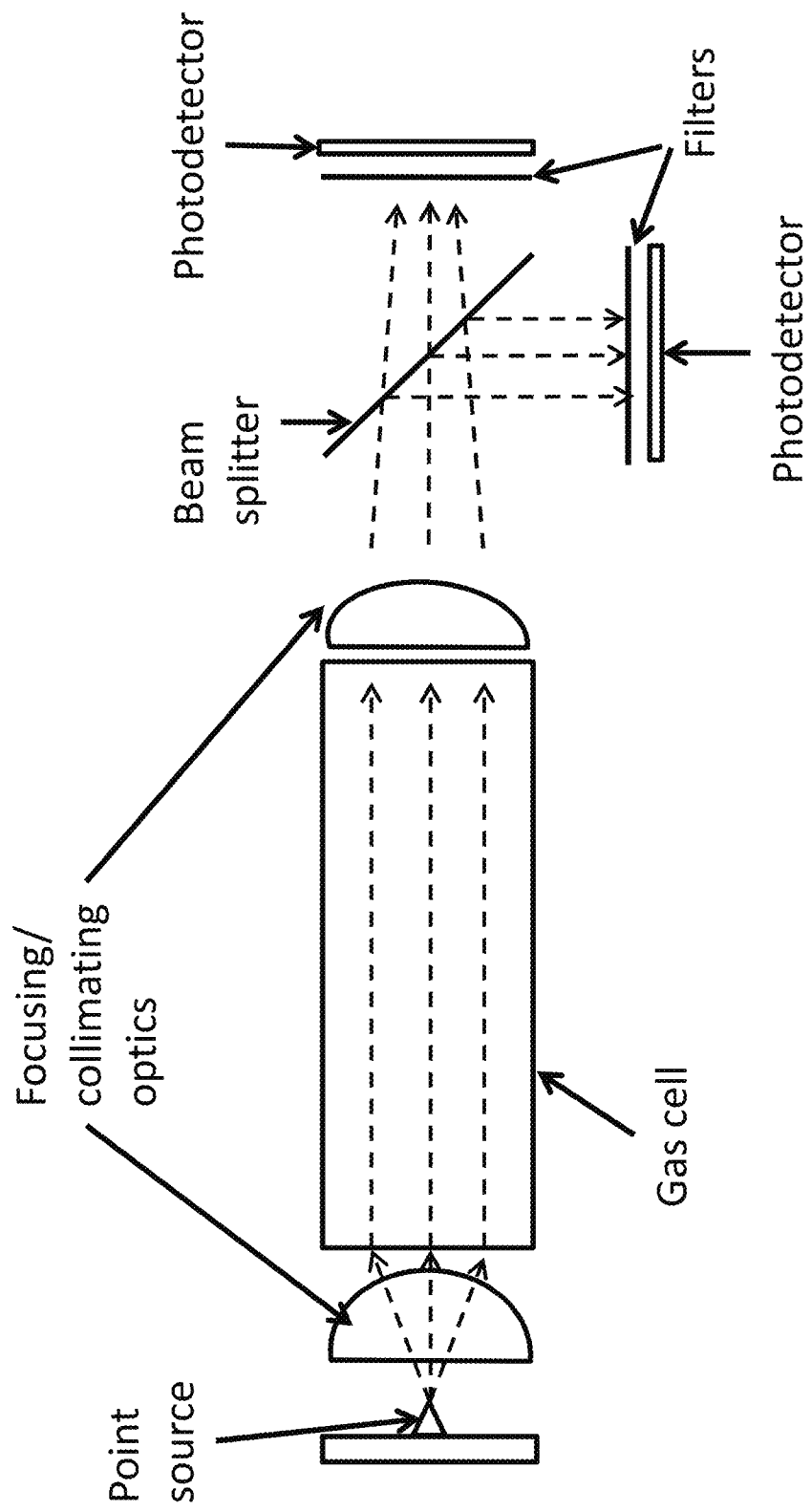
FIG. 7 is a prior art schematic of a conventional NDIR gas sensor for single gas sensing with a separate calibration detector.

A gas sensor can use the emitter 100 to provide infrared radiation for detection of specific gas species. FIG. 7 illustrates a system schematic of a conventional NDIR gas sensor. Conventional NDIR gas sensors typically use a point light source. Therefore, collimating and focusing optical components have to be used to produce parallel light beams through the gas cell for the most efficient use of the emitted light. To calibrate the conventional system, the light beam is split by using a beam splitter. The separate beams then pass through narrow band-pass filters and are detected at separate photodetectors. The depicted configuration is used for detection of a single gas species with a calibration functionality. For multi-gas detection, multiple gas sensor cells would be required with band-pass filters matching each of the characteristic absorption bands of the multiple species of gas molecules that are to be detected.

Figure 8:
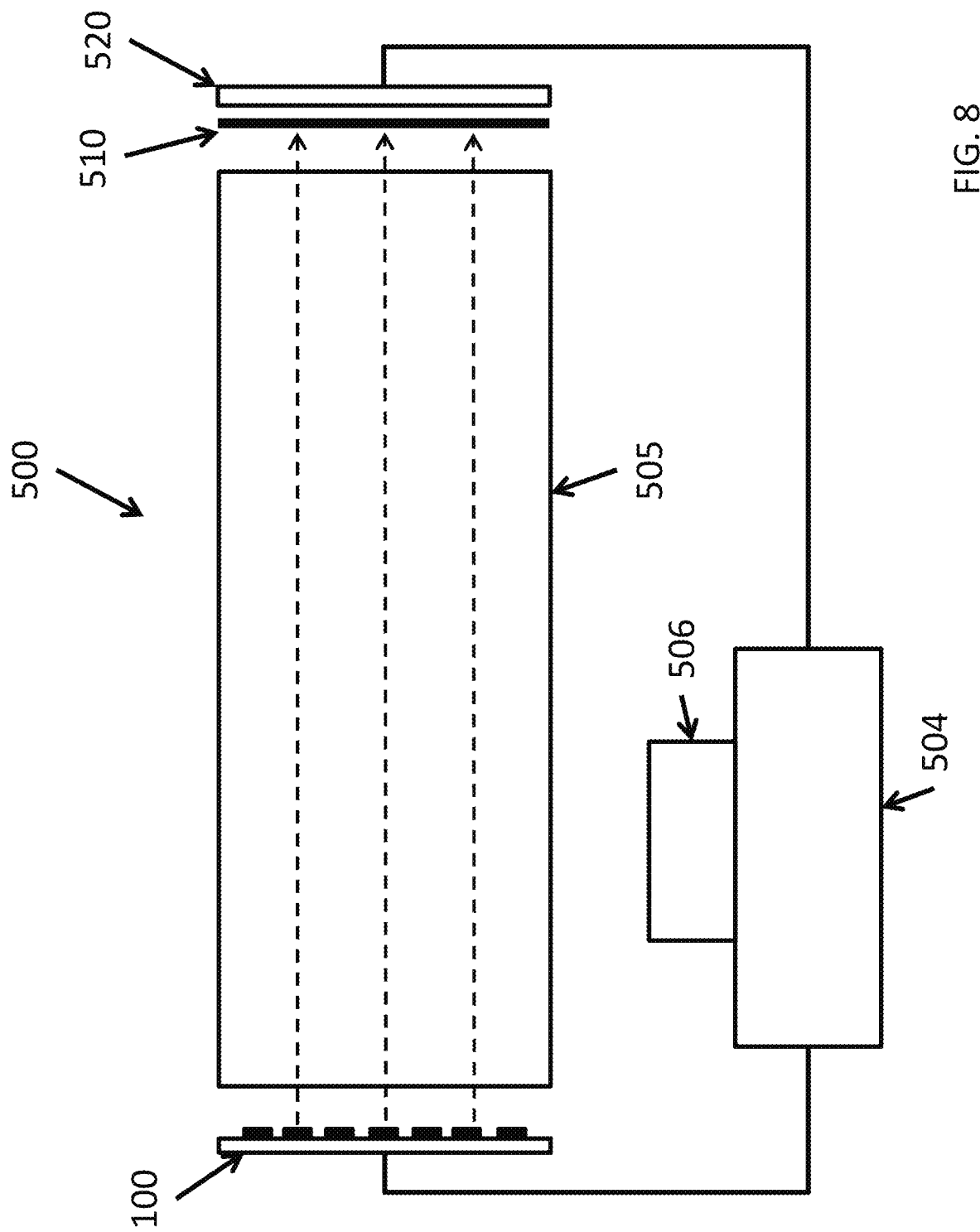
FIG. 8 is a schematic of the NDIR gas sensor according to various embodiments of the present invention with built-in calibration functionality and multi-gas sensing capabilities.

FIG. 8 illustrates a system schematic of an NDIR gas sensor 500 according to various embodiments described herein. The gas sensor 500 includes the emitter 100, a gas cell 505, a broadband optical filter 510, and a photodetector 520. The emitter 100 can emit a collimated light beam at multiple narrow bandwidth peak wavelengths as described above with reference to, for example, FIG. 2 and FIG. 3. The emitter can be controlled by a control circuit or microcontroller within data processor system 504 that can include one or more processors that perform control and data processing functions. One or more memories can be used to store data from detector 520. Data can be displayed on electronic display 506. Because the light beam size is determined by the active area of the membrane layer 102, the size of the beam can easily be matched with a cross-sectional area of the gas cell 505 without using extra optical components. Advantageously, the NDIR gas sensor 500 does not require a costly narrowband band-pass filter to discriminate signals from out-of-band emissions. In some embodiments, the low-cost broadband filter 510 can be used to eliminate background noise and saturation of the photodetector 520. As shown, the gas sensor 500 does not require collimating and focusing optical components, high cost narrowband band-pass filters, or a second photodetector for sensor calibration. Advantageously, sensing of multiple gas species simultaneously is feasible by detecting light traveling through a single gas cell 505 from the emitter 100 to the photodetector 520. As a result, the gas sensor 500 is more compact and requires less electrical power than conventional systems.

FIGS. 9a and 9b show schematics of on-board NDIR gas sensor systems 900, 900', respectively, of the current invention. The on-board gas sensor system 900 can be provided affixed or mounted directly onto a substrate 950 such as a printed circuit board (PCB) to enable direct integration into portable microelectronic devices using traditional techniques such as pick-and-place.

The gas sensor system 900 includes the emitter 100, a gas cell 905, and a photodetector 920. The emitter 100 can be directly mounted onto the substrate 950 (e.g., PCB) via surface mounting. As depicted in FIG. 9A, the emitter 100 emits in a direction perpendicular to a surface of the substrate 950. The parallel light beam from the emitter is reflected by a reflective surface 912 in the gas cell 905, passes through the gas cell 905 while colliding with gas molecules, and reflects from a reflective surface 912 onto the photodetector 920. In accordance with various embodiments, the emitter 100 or photodetector 920 can be located within the gas cell 905.

In some embodiments, the gas cell 905 can be clipped onto the substrate 950 using a gas-tight seal at the interface for ease of assembly. In some embodiments, the gas cell 905 of the gas sensor system 900 can include one or more reflective surfaces 912 to reflect or direct emitted light on an optical path from the emitter to the photodetector 920. The reflective surfaces 912 can be produced by metallizing interior surfaces of the gas cell 905 in some embodiments. The gas cell 905 can have gas inlets 915 in some embodiments. The gas inlets 915 can facilitate gas exchange between the interior of the gas cell 905 and the exterior environment in some embodiments. The gas inlets 915 can optionally include particle filters. In some embodiments, the walls of the gas cell 905 can include a thermoplastic suitable for use in injection molding.

The stand-alone gas sensor system 900' illustrated in FIG. 9b includes the emitter 100, gas cell 905, and photodetector 920 each of which may be attached to the substrate 950 (e.g., printed circuit board or PCB) or other system peripherals. As shown, the emitter 100 of the gas sensor system 900' can emit in a direction parallel to the surface of the substrate 950. The gas cell 905 can include gas openings 915 in some embodiments. The gas openings 915 can include particle filters to filter out particles during gas exchange. The gas openings 915 can facilitate gas exchange between the interior of the gas cell 905 and the exterior environment in some embodiments. In some embodiments of the stand-alone gas sensor system 900', the plasmonic emitter 100 and the photodetector 920 can be directly attached to opposite ends of a housing of the gas cell 905. The housing can be formed using injection molded plastic in some embodiments.

Figure 10:
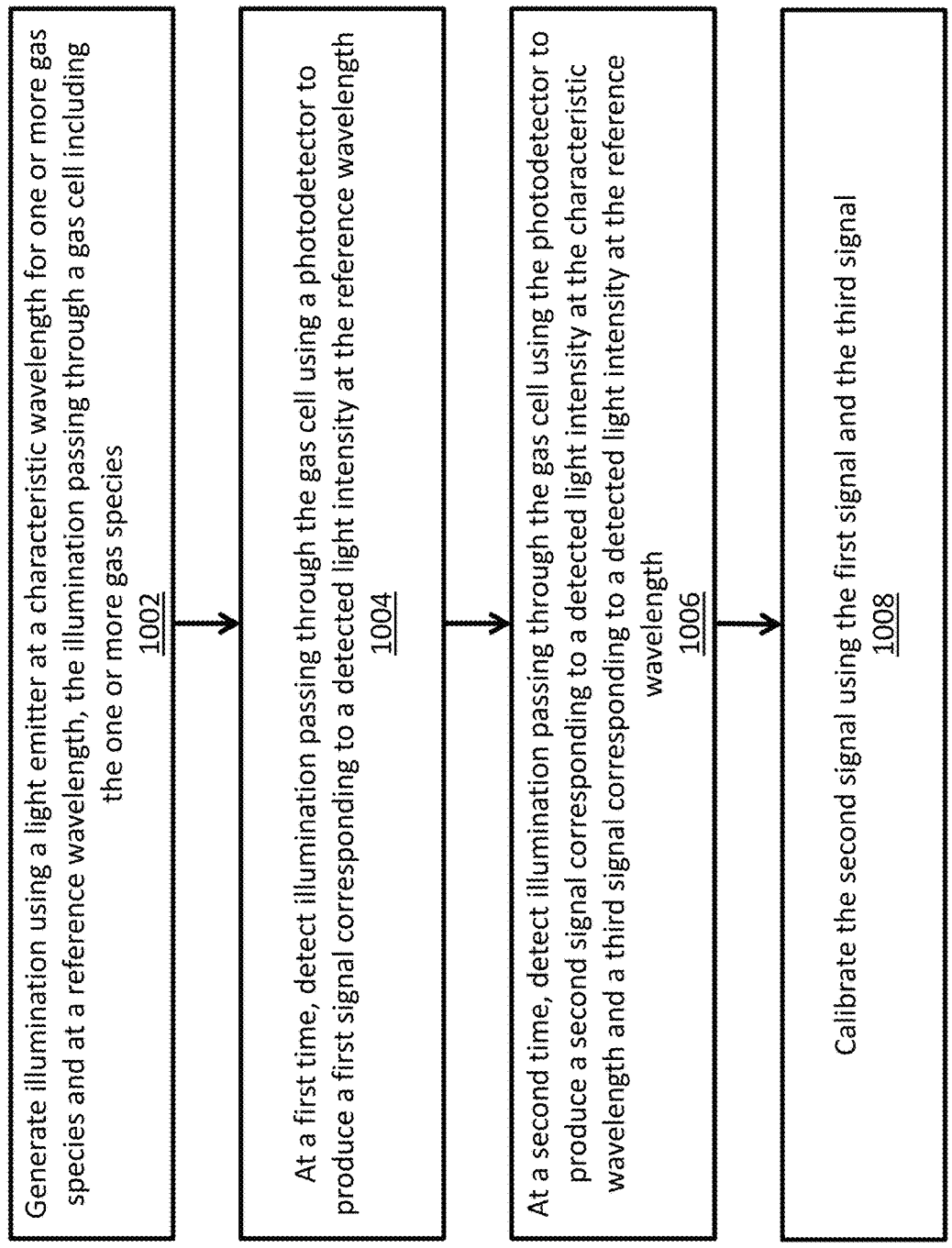
FIG. 10 shows a flowchart illustrating a method 1000 for calibration of a gas sensor in real time in accordance with various embodiments described herein.

FIG. 10 shows a flowchart illustrating a method 1000 for calibration of a gas sensor in real time in accordance with various embodiments described herein. The method 1000 includes generating illumination using a light emitter at a characteristic wavelength for one or more gas species and at a reference wavelength (step 1002). The illumination passes through a gas cell including the one or more gas species. For example, the emitter 100 can be used to emit dual peak radiation through the gas cell 505 as described above. The method 1000 includes detecting, at a first time, illumination passing through the gas cell using a photodetector to produce a first signal corresponding to a detected light intensity at the reference wavelength (step 1004). For example, the photodetector 520 can detect the light and transmit the signal to a data processor system 504 as described above.

The method 1000 includes detecting, at a second time, illumination passing through the gas cell using the photodetector to produce a second signal corresponding to a detected light intensity at the characteristic wavelength and a third signal corresponding to a detected light intensity at the reference wavelength (step 1006). The method 1000 includes calibrating the second signal using the first signal and the third signal (step 1008). For example, the second signal can be multiplied by a quotient of the first signal and the third signal in some embodiments.

Figure 11:
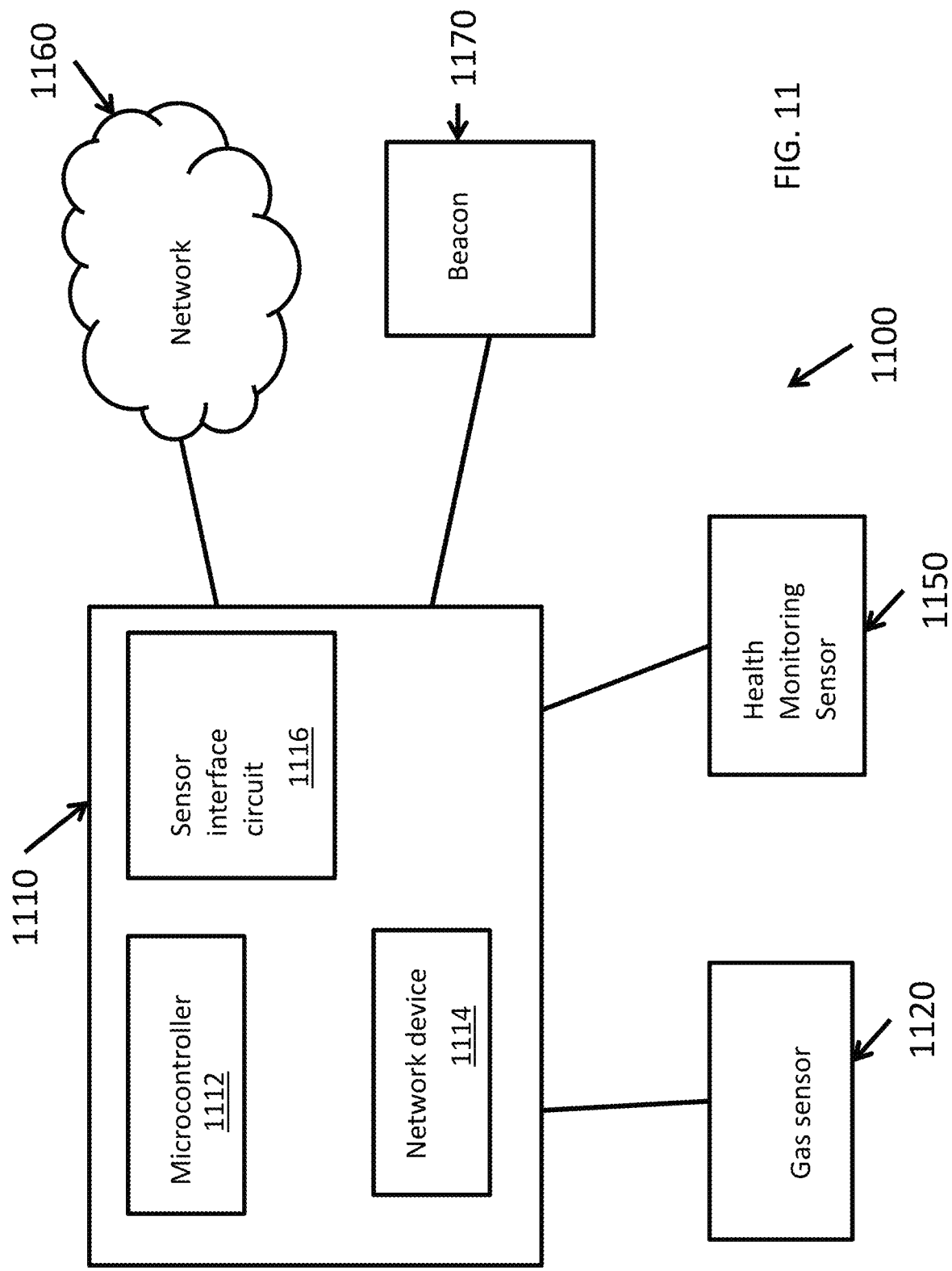
FIG. 11 illustrates a system for health monitoring in accordance with various embodiments described herein.

Gas sensors of the present disclosure are robust and require low amounts of electrical power to operate. As such, they are suitable for use in a variety of point-of-care, mobile, or wearable applications where compact, robust packaging and power consumption are paramount concerns. FIG. 11 illustrates a system 1100 for health monitoring in accordance with various embodiments described herein. The system 1100 includes a controller 1110 having a microcontroller 1112, a network device 1114, and a sensor interface circuit 1116. The controller 1110 is communicatively coupled to a gas sensor 1120, one or more health monitoring sensors 1150, a network 1160, and a beacon 1170. In some embodiments, the system 1100 can gather health information from a patient and relay the health information to a central location using the network 1160.

The gas sensor 1120 of some embodiments can be one of the gas sensors 500, 900, 900' as described above. The gas sensor 1120 includes the plasmonic emitter 100 described previously. The gas sensor 1120 can be a separate component that is communicatively coupled to the controller 1110 in some embodiments. In other embodiments, the gas sensor 1120 can be integrated directly into the controller 1110. For example, the gas sensor 1120 can be integrated onto the same printed circuit board as the microcontroller 1112 in some embodiments.

The gas sensor 1120 can be used in various embodiments to perform measurements on a sample of the patient's breath. The patient can exhale into the gas sensor 1120 to conduct a measurement. In some embodiments, the system 1100 can prompt the patient to breathe into the gas sensor 1120 at regular intervals or based upon receipt of a notification or prompt from the network 1160. In some embodiments, the gas sensor 1120 can measure the absolute or relative concentrations of compounds within the patient's breath. The compounds can include volatile organic compounds (VOCs) in some embodiments.

The one or more health monitoring sensors 1150 can include sensors to measure a variety of health indicators on a patient. In various embodiments, the health monitoring sensors 1150 can measure body temperature, electrocardiogram, air flow, pulse rate, blood oxygenation, blood pressure, light, body orientation, or body impacts. The health monitoring sensors 1150 can include a fall sensor to detect when a patient has fallen down.

The controller 1110 includes a sensor interface circuit 1116 to communicate with and control the gas sensor 1120 and/or the health monitoring sensors 1150 in various embodiments. For example, the sensor interface circuit 1116 can send control signals or data to the gas sensor 1120 or health monitoring sensors 1150 and can receive data or self-diagnostic results from the gas sensor 1120 or health monitoring sensors 1150. In some embodiments, the microcontroller 1112 can include a Raspberry Pi device.

The network device 1114 can enable the controller 1110 to communicate with external devices or networks. The network device 1114 can communicate using a variety of communications protocols including the various 802.11x standards, Wi-fi, Bluetooth™, near-field communications technologies, or any other suitable communication protocol. For example, the network device 1114 can communicate with a network 1160 to send or receive data such as patient identification information or health information. The network 1160 can be a Local Area Network (LAN), a Wide Area Network (WAN), or the Internet in whole or in part. In some embodiments, the network device 1114 can communicate with the beacon 1170. In some embodiments, the communication can employ technology that is proximity-dependent in some respect such as near-field communications (i.e., RFID) or Bluetooth™ devices. Communication with the beacon 1170 can establish the physical location of the controller 1110 and/or sensors 1120, 1150 within a space. In some embodiments, the beacon can include a device compatible with the iBeacon protocol developed by Apple Corporation (Cupertino, Calif.).

In some embodiments, the controller 1110 and/or sensors 1120, 1150 can be worn by the patient to enable continuous monitoring of patient health indicators while providing the patient freedom of movement. In some embodiments, the controller 1110 and/or sensors 1120, 1150 can be embedded into clothing worn by the patient.

Figure 12:
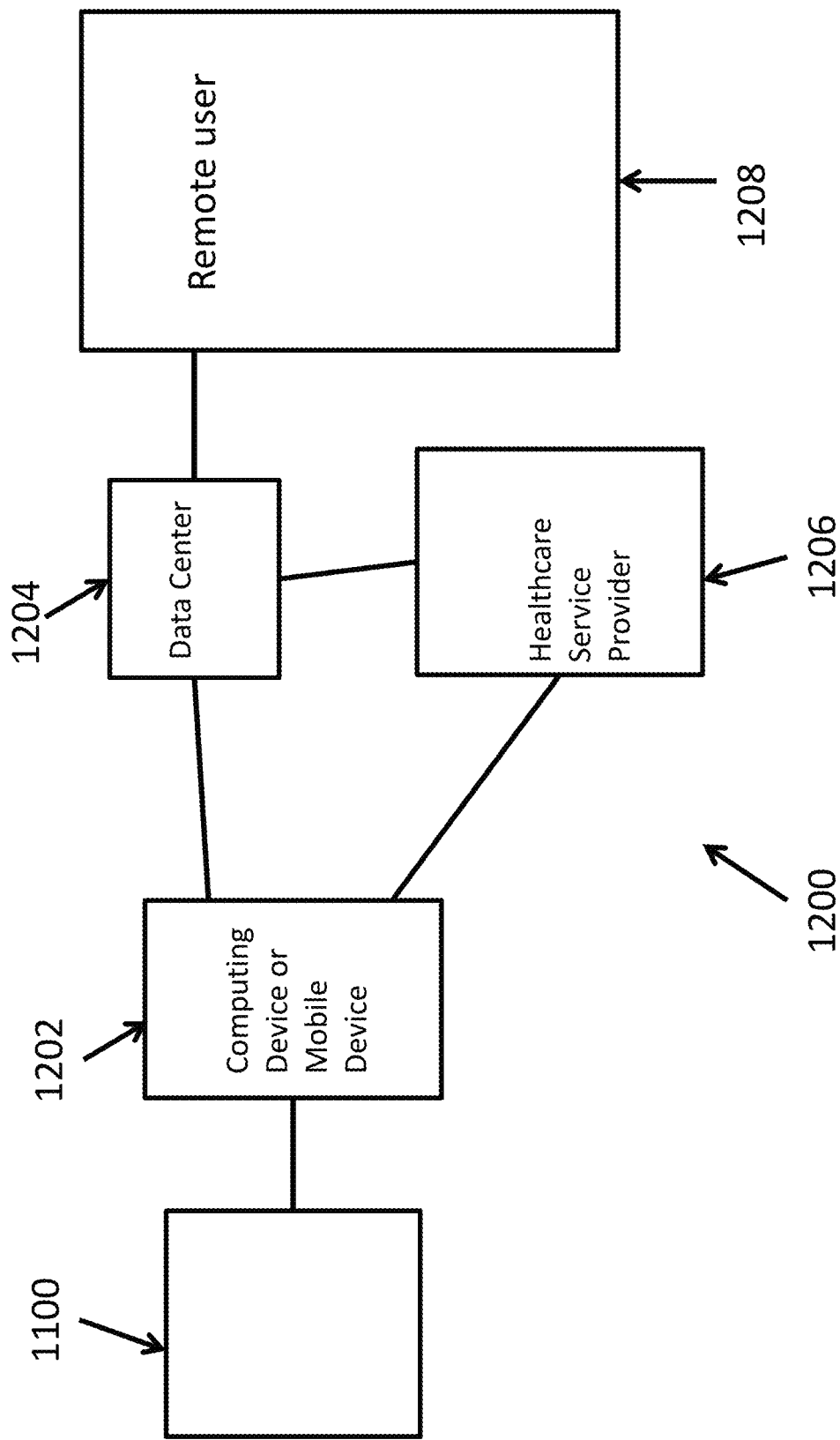
FIG. 12 illustrates a framework for monitoring and recording patient health including the system of FIG. 11 according to various embodiments described herein.

As shown in FIG. 12, the system 1100 can be part of a larger framework 1200 to monitor and record patient health. The system 1100, which can include smart clothing in some embodiments, can transmit data to computing device 1202. The computing device 1202 can include a communication gateway, a server, or a mobile device such as a mobile telecommunications device (e.g., mobile phone) or tablet computer. The handheld mobile computing device 1202 can comprise a wired or wireless connection to system 1100 as described herein, or to a cellular communication network. Device 1202 can comprise an electronic display, a processor, a wireless transceiver and a memory that stores data received and processed by mobile device 1202. The system 1100 can transmit the information to the computing device 1202 using the network 1160 as described previously. The system 1100 or computing device 1202 can be used to transmit the information to a central health data center 1204 in some embodiments. The data center 1204 can be cloud-based in some implementations.

A healthcare service provider 1206 can access the data from the data center 1204 or from the computing device 1202. Remote users 1208 that are authorized can also access the data in the data center 1204. In some embodiments, the remove users can include medical advisors, immediate family of the patient, or emergency medical services. For example, family or EMS can monitor data in the data center 1204 to identify changes in the data that could indicate an emergency condition. In some embodiments, the framework 1200 can automatically summon emergency services or push a notification to a remote user 1208 to warn that measured health indicator values for the patient have exceeded or dropped below a threshold.

Figure 13A:
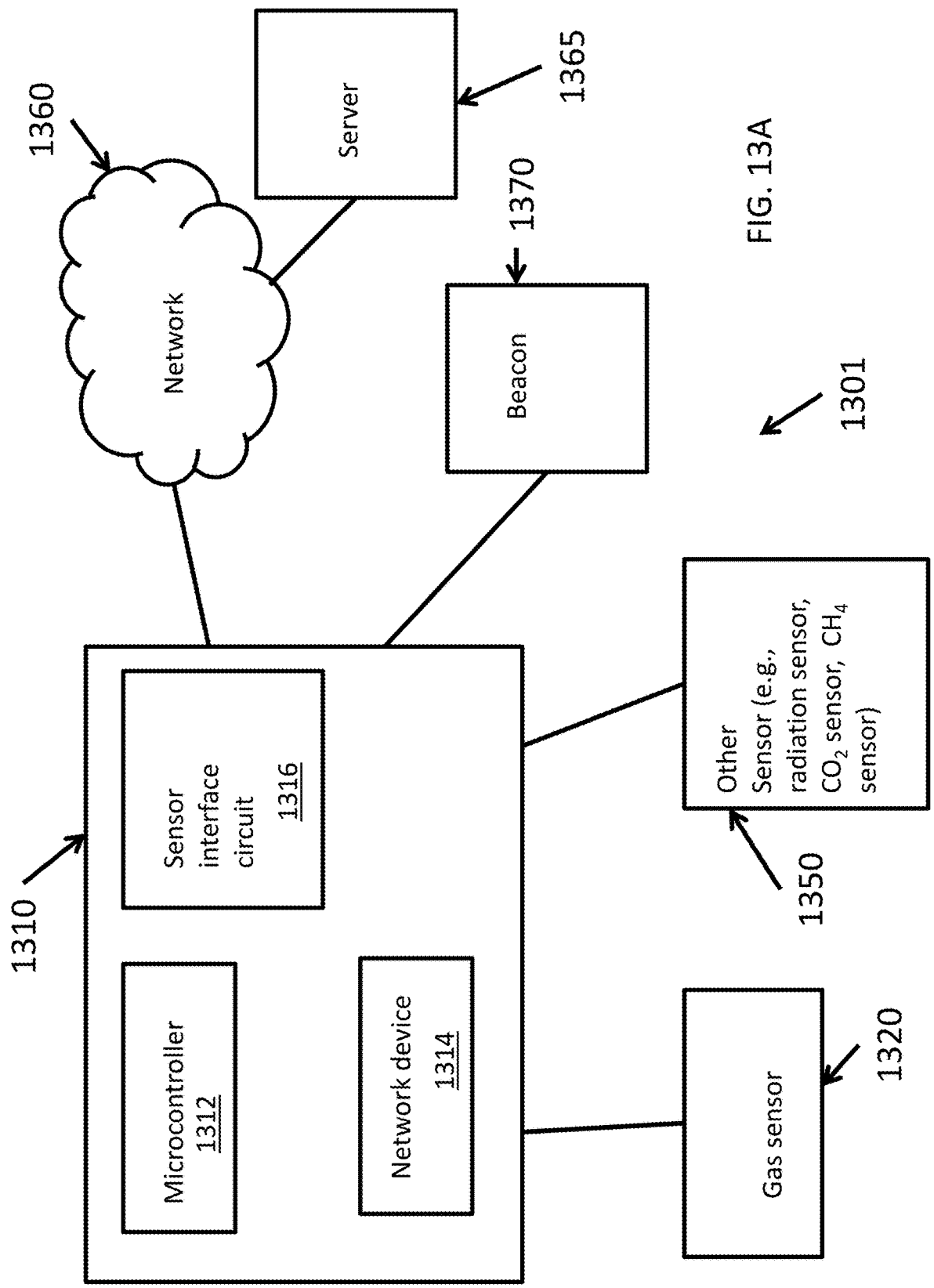
FIG. 13A illustrates a system for environmental monitoring in accordance with various embodiments described herein.
Figure 13B:
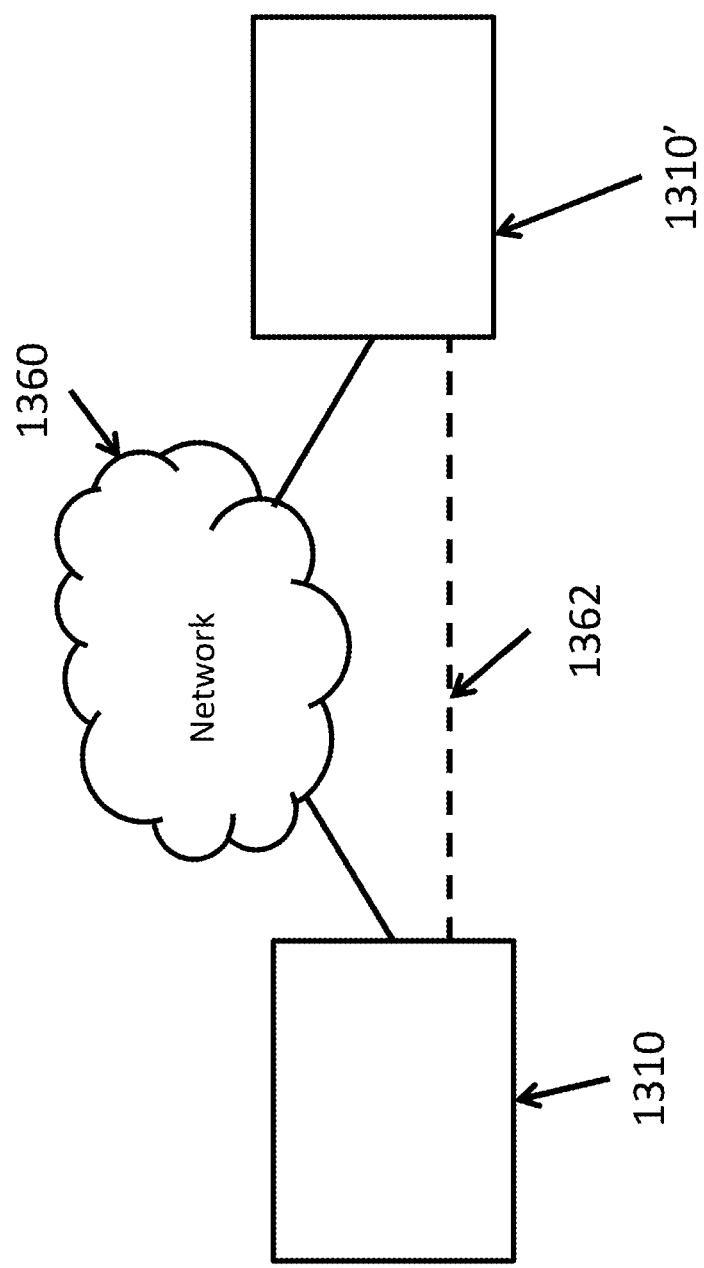
FIG. 13B illustrates communication among multiple controllers in the system for environmental monitoring in accordance with various embodiments described herein.

FIG. 13A illustrates a system 1301 for environmental monitoring and location sensing in accordance with various embodiments described herein. The system 1301 includes a controller 1310 having a microcontroller 1312, a network device 1314, and a sensor interface circuit 1316. The controller 1310 is communicatively coupled to a gas sensor 1320, a network 1360, a beacon 1370, and one or more other sensors 1350 including, but not limited to, a radiation sensor, a carbon dioxide sensor, and a methane sensor. The system 1301 can include a server 1365 in communication with the network 1360. As illustrated in FIG. 13B, the system 1301 can include multiple controllers 1310, 1310'. Each of the controllers 1310, 1310' can be aware of its spatial location with respect to at least one of the other controllers 1310, 1310', with respect to waypoints in physical space, or both. In some embodiments, the system 1301 can place controllers 1310, 1310' at different locations in physical space to gather information about environmental conditions at the different locations and deliver that information to a central location using the network 1360.

In some embodiments, each controller 1310 in the system 1301 can communicate with other controllers 1310' through the network 1360 or through a direct peer-to-peer communication link 1362. The direct peer-to-peer communication link 1362 can enable exchange of information between controllers 1310, 1310' in the system 1301. The direct peer-to-peer communication link 1362 can be wireless in an exemplary embodiment. In some embodiments, the controllers 1310, 1310' can determine whether to send sensed data (e.g., gas sensor data or radiation data) directly to server 1365 through the network 1360 or through intermediaries such as other controllers 1310, 1310'. For example, one controller 1310 may have a stronger signal connection to the network 1360 owing to closer proximity to a beacon 1370 or other factors such as greater signal-to-noise due to fewer multipath reflections from surrounding objects. In such a case, the controllers 1310, 1310' can send data payloads including sensor data to the controller 1310, 1310' having the strongest connection to the network 1360. In some embodiments, the peer-to-peer communication link 1362 can enable determination of spatial locations for controllers 1310, 1310' with respect to one another.

Exemplary methods and systems for determining the distance between controllers 1310, 1310', for example, using broadcast messaging are described in U.S. Pat. No. 9,983, 292 issued May 29, 2018 to Hach et al. and U.S. Pat. No. 7,843,379 issued Nov. 20, 2010 to Menzer et al. The entire contents of each of these patents are hereby incorporated herein by reference. The controllers 1310, 1310' can form a plurality of interconnected nodes that are spatially aware and can sense and monitor environmental conditions at different spatial locations. Communications between and among controllers 1310, 1310' or between controllers 1310, 1310' and the network 1360 can include both sensed data and location-determination data in each packet or data payload in some embodiments. As described in the aforementioned patents, the controllers and sensor devices described herein can be mounted within, or communicatively connected at the same location as, tags and/or anchors so as to transmit and receive broadcast messages (by radio frequency (RF) or other wireless transmission and reception methodologies and devices) including both sensor data and time of flight/time of arrival (TOA) and/or time distance of arrival (TDOA) measurements to compute real-time location data. The server 1365 can act as a location server or data processor system that can compute position information and store co-located sensor data as generally described herein. Thus, sensor data (e.g., from any of the gas sensor, radiation sensor, carbon dioxide sensor, methane sensor, etc.) can be transmitted in the same packet with contemporaneous position data. The location tags can comprise battery operated wireless mobile devices that can be tracked, or which can be affixed to larger robotic structures or systems, for example, such as construction equipment which can optionally provide power to one or more location tags.

In some embodiments, each controller 1310, 1310' is attached to a mobile platform such as an autonomous or semi-autonomous drone or robotic system to enable movement in free space. The mobile platforms can enable controllers 1310, 1310' to move with respect to on another in some embodiments. In some embodiments, the system 1301 can dispatch one or more controllers 1310, 1310' to move toward a potential environmental danger. For example, if one controller 1310 senses elevated readings of environmental factors such as radiation or noxious gases, the controller 1310 can move in a direction that causes subsequent readings of the environmental factor to increase. Multiple mobile controllers 1310, 1310' can be deployed in some embodiments. The system 1301 can direct the one or more controllers 1310, 1310' to perform a bracketing maneuver to attempt to pinpoint the accessible location with the largest value for the environmental factor as this can be presumed to be closest to the source of the environmental factor.

The one or more other sensors 1350 can include a radiation sensor. The radiation sensor can be a floating gate dosimeter (FGD-02F, Sealicon Microsystems, Integrated Circuits Malaga SI, Mallorca, Spain) in some embodiments. The one or more other sensors 1350 can include low power carbon dioxide or methane sensors in some embodiments. For example, the low-power carbon dioxide and methane sensors can operate using light-emitting diode (LED) light sources, sometimes in combination with spectral filters to narrow the emission bandwidth. For example, the low power carbon dioxide sensor can be the CozIR®-LP or CozIR®-A $CO_2$ sensors (Gas Sensing Solutions, Cumbernauld, United Kingdom). In some embodiments, the methane sensor can be the MIPEX-04 (Mipex Technology, St. Petersburg, Russia). Such sensors can be mounted with global positioning system (GPS) devices or, if the sensor devices or arrays are located or move within a GPS-denied environment such as indoors within building structures or underground within tunnels and mines, radio frequency (RF) messaging systems can be used. Exemplary real-time location system (RTLS) devices can be obtained from Nanotron Technologies GmbH, Berlin, Germany including tags, anchors, location servers, and software that processes "chip" signaling messages from a plurality of tags, up to hundreds or thousands thereof, simultaneously. Such communication networks can also include wireless transceivers that operate with ultra-wideband (UWB) devices available from Decawave Ltd., Dublin, Ireland. The DW1000 transceiver integrated circuit can be incorporated into controllers 1310, 1310' (such as location tags and/or anchor devices) along with sensors (e.g., gas sensor 1320 and other sensors 1350) to send location and sensor data.

Figure 14:
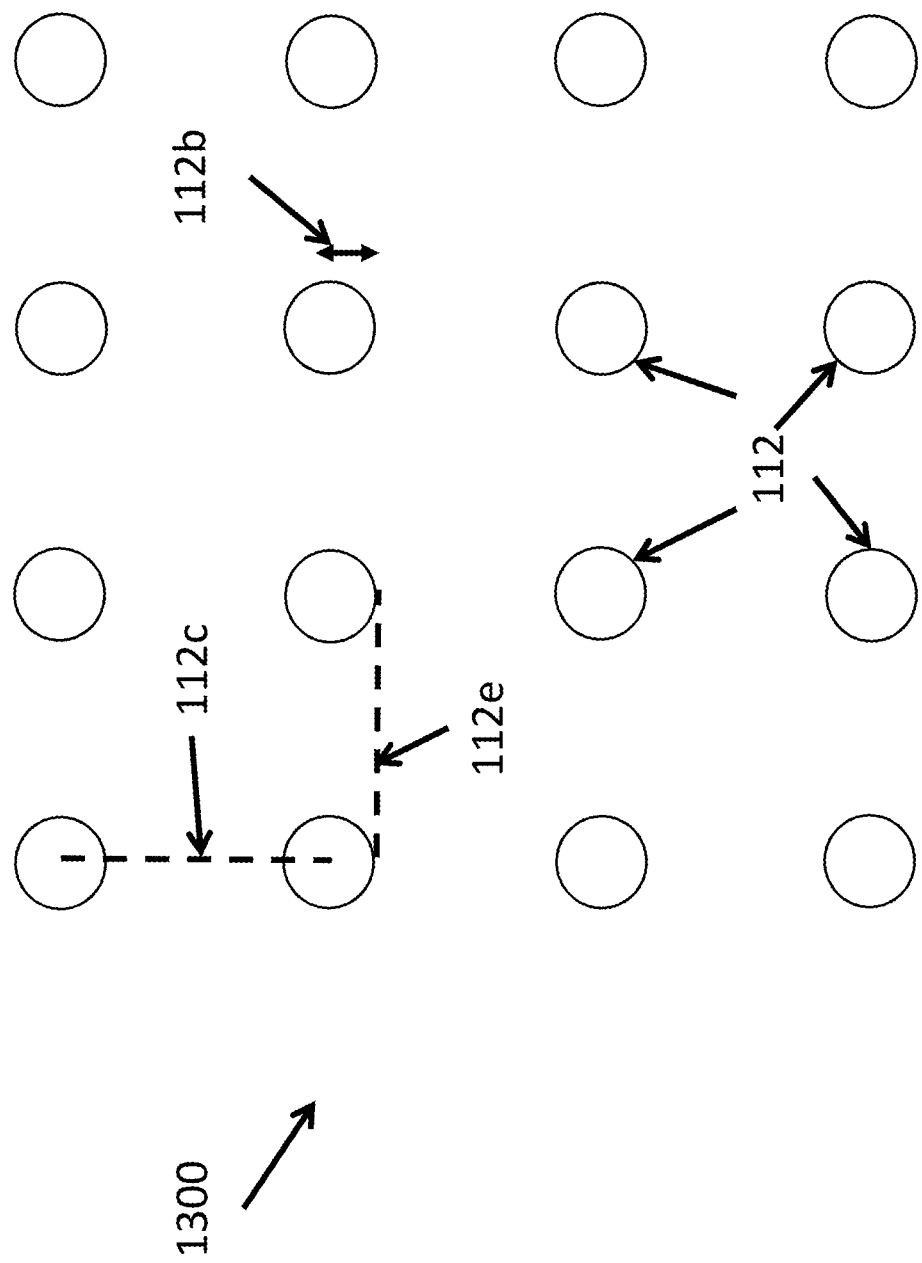
FIG. 14 illustrates an exemplary pattern for relief features in a patterned conductive layer in accordance with various embodiments described herein.

FIG. 14 illustrates a top view of a pattern 1300 for the relief features 112 in the patterned conductive layer 110 in accordance with various embodiments. As described above with respect to FIG. 1, the relief features 112 can be separated from one other by the pitch 112*c*. In some embodiments, the pitch can vary in two-dimensions. In other words, the relief features 112 can be separated by a first pitch 112*c* in a first direction and by a second pitch 112*e* in a second direction in some embodiments. In some embodiments, the first direction and the second direction can be orthogonal. In other embodiments, the first direction and the second direction can be at non-orthogonal angles. The first and second directions can be chosen to correspond to certain crystal or lattice parameters in some embodiments.

Figure 15:
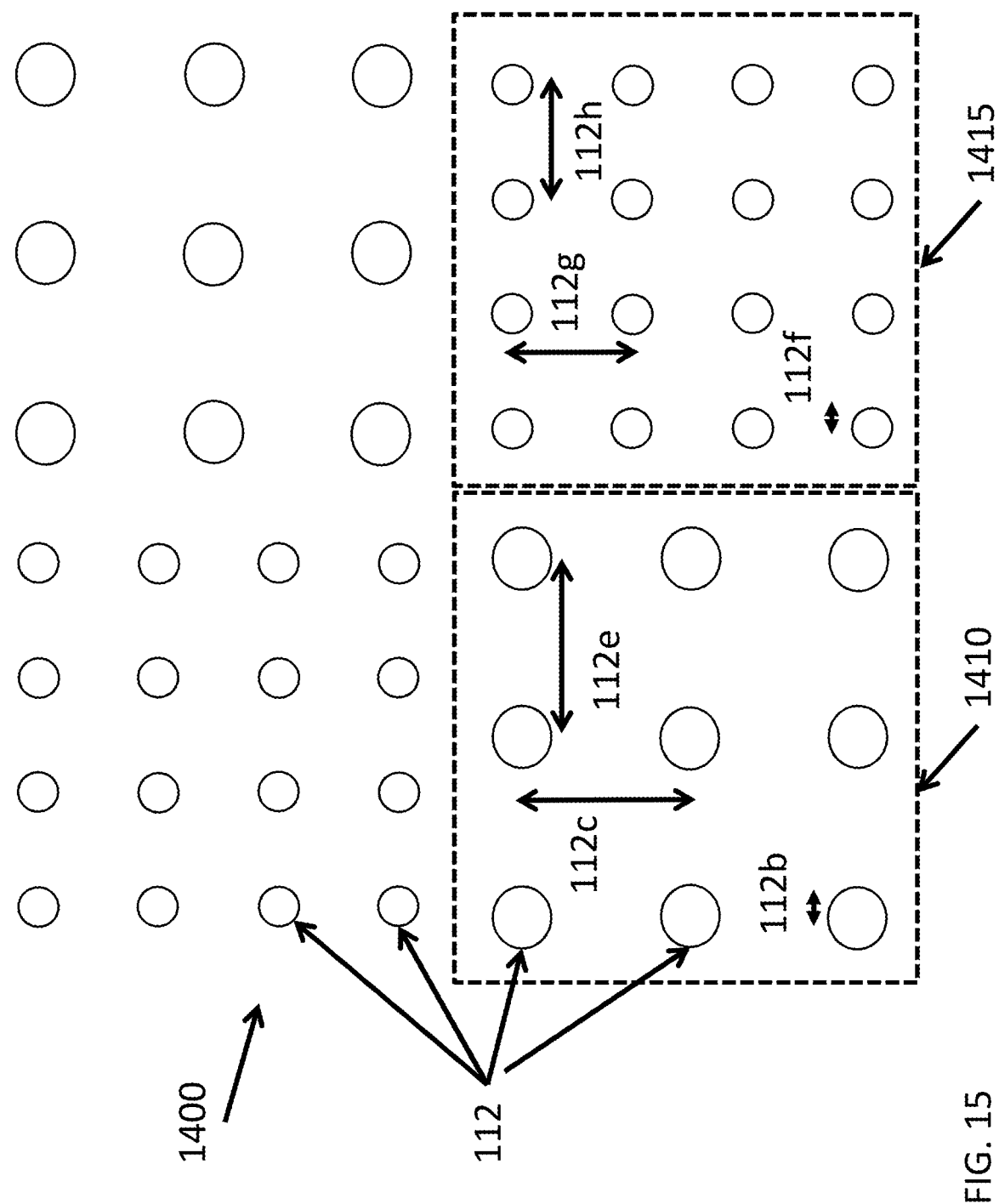
FIG. 15 illustrates an exemplary supercell pattern for relief features in a patterned conductive layer in accordance with various embodiments described herein.

FIG. 15 illustrates a top view of a supercell pattern 1400 for the relief features 112 in the patterned conductive layer 110 in accordance with various embodiments. The supercell pattern 1400 can include repeated short-range-order patches 1410, 1415 of relief features 112 in some embodiments. Although two short-range-order patches 1410, 1415 are illustrated, one of ordinary skill in the art would appreciate that any number of patches can be included in a supercell pattern 1400. In some embodiments, the patches 1410, 1415 can be arranged in a cubic (e.g., checkerboard) pattern to form the supercell pattern 1400. In other embodiments, the supercell pattern 1400 can include patches 1410, 1415 that are organized in any known tessellation arrangement such as hexagons, triangles, Penrose patterns, Truchet tilings, Voronoi tilings, Dirichlet tilings, or others. The different patches 1410, 1415 do not need to have identical lengths, sizes, or shapes to one another. By using a supercell pattern 1400, multiple narrow bandwidth peaks can be produced via near-field interference between the short-range-order patches 1410, 1415.

Each short-range-order patch 1410, 1415 includes relief structures 112 having different lateral dimensions 112*b*, different pitches 112*c*, 112*e* in one or more directions, or both. For example, relief structures 112 in the first short-range-order patch 1410 can have a first lateral dimension 112*b* and relief structures 112 in the second short-range-order patch 1415 can have a second lateral dimension 112*f* different from the first lateral dimension 112*b*. Similarly, relief structures 112 in the first short-range-order patch 1410 can be separated by the pitch 112*c* in the first direction and the pitch 112*e* in the second direction while relief structures 112 in the second short-range-order patch 1415 can be separated by a pitch 112*g* in the first direction and a pitch 112*h* in the second direction. The pitches 112*c*, 112*e* can differ from pitches 112*g*, 112*h*.

Figure 16:
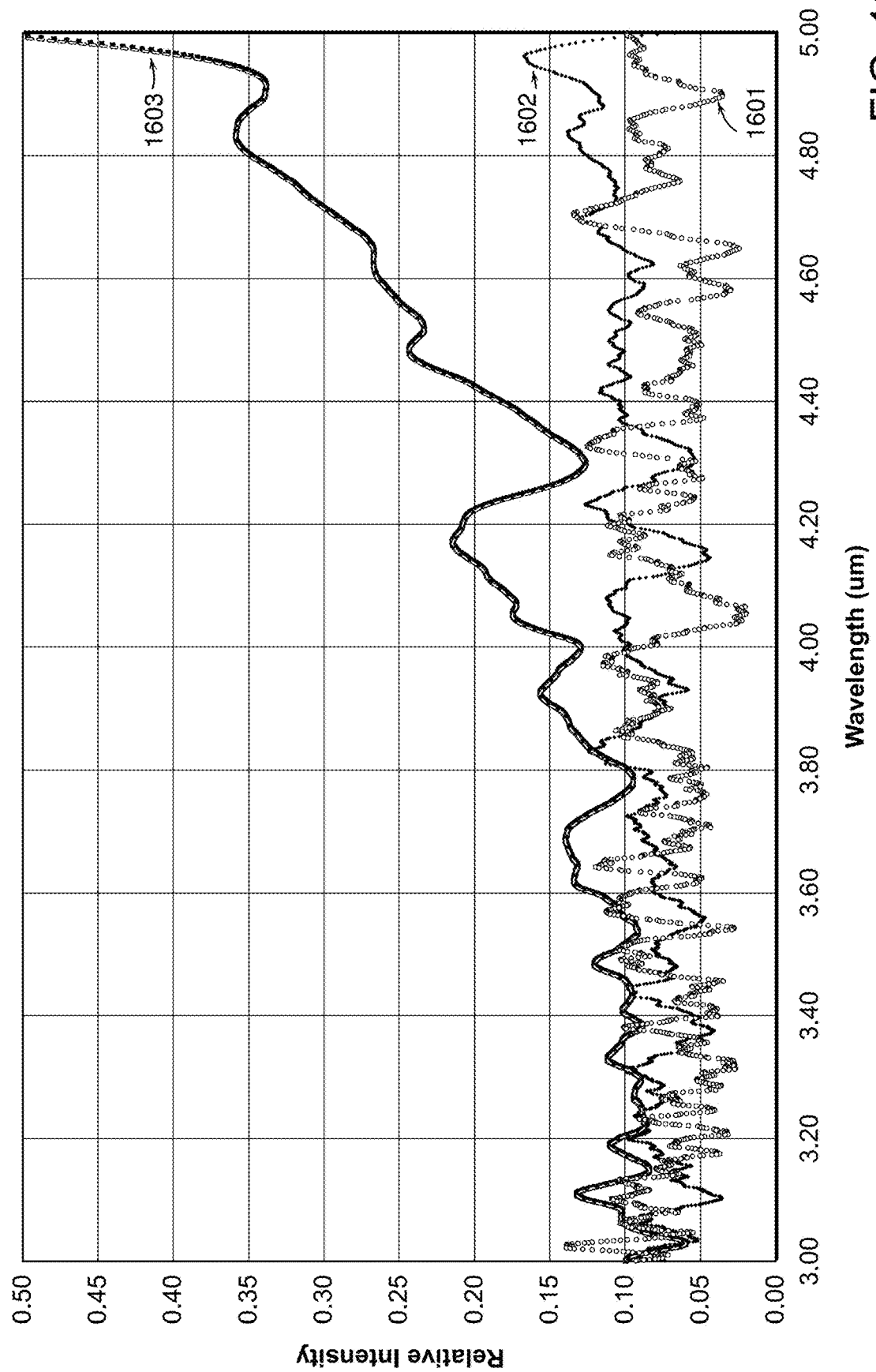
FIG. 16 illustrates measured background optical outputs of various heater strips.

FIG. 16 shows background optical outputs as relative intensity from various heater strips in accordance with various embodiments herein. Trace 1601 corresponds to a thin film heater strip without heating. Trace 1602 corresponds to a thin film heater strip having membrane layer thickness less than 5 µm under pulsed power heating. Trace 1603 corresponds to a thick film heater strip having membrane layer thickness of about 475 µm under pulsed power heating. The heater strips in these measurements had non-patterned conductive layers (i.e., no plasmonic emitter pattern). The optical output was measured using a Fourier-transform infrared spectroscopy (FTIR) spectrometer (Model No. M500, Buck Scientific, Inc., E. Norwalk, Conn.). To measure the optical output of the heater strips, the blackbody light source in the FTIR spectrometer was replaced with the heater strips.

The heater strips were heated under various pulsed electric power conditions, which were generated using an LDD-1124-SV Laser Diode Driver (Meerstetter Engineering GmbH, Rubigen, Switzerland). For heater strip heating, a pulsed power input of 18 ms ON and 2 ms OFF was repeated for 30 minutes before conducting measurements of the optical output. For all background optical output measurements, background noise was reduced using a spectral smoothing function available in the FTIR spectrometer.

As shown in FIG. 16, there is no heater strip heating without electric power input, indicated by flat optical output of trace 1601. For the thin film strip heater (trace 1602), a slight increased in the background level below 4.6 µm was observed upon heating the thin film heater strip using the pulsed electric power for 30 minutes. Significant heating of the thick film heater strip (trace 1603) was observed as indicated by increased optical output at longer wavelengths.

Figure 17:
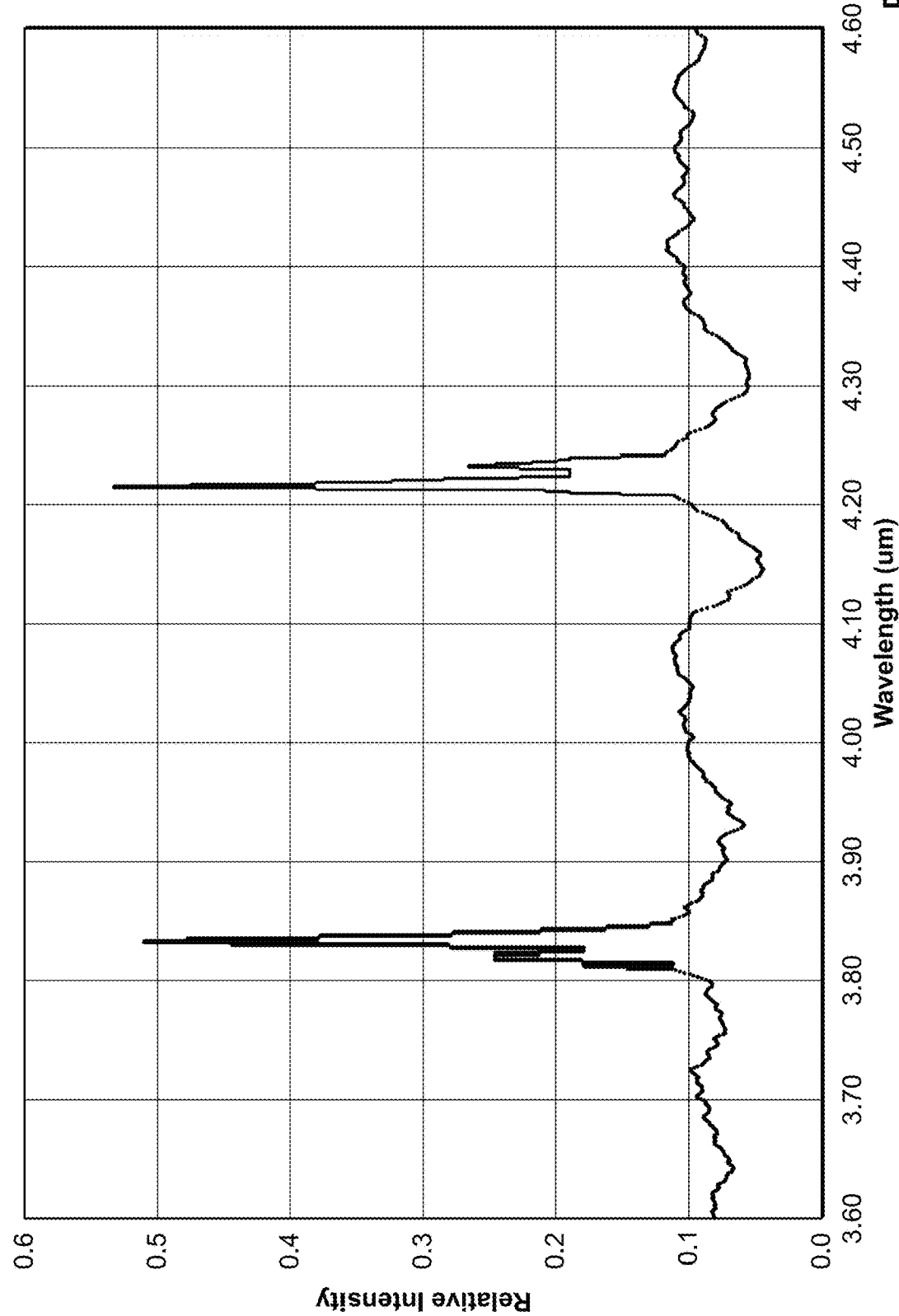
FIG. 17 illustrates measured emission peaks of the thin film plasmonic IR emitter with a patterned conductive layer designed for dual emission peaks at 3.85 μm and 4.26 μm.

FIG. 17 illustrates the optical output as relative intensity for the thin film heater strip with a patterned conductive layer on the top. The measurement includes two emission peaks, i.e., peaks at nominal wavelengths of 3.85 µm (the reference peak) and 4.26 µm (the carbon dioxide peak). A pulsed electric power input of 18 ms ON and 2 ms OFF was used to generate the dual peak emissions. As shown, both peaks were not symmetrical. The measured peak positions were 3.83 µm and 4.23 µm for the reference and carbon dioxide peaks, respectively. The peak positions were very close to the simulated values and were shifted only 20-30 nm to shorter wavelength for both peaks.

While the present inventive concepts have been described with reference to particular embodiments, those of ordinary skill in the art will appreciate that various substitutions and/or other alterations may be made to the embodiments without departing from the spirit of the present inventive concepts. Accordingly, the foregoing description is meant to be exemplary and does not limit the scope of the present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

The invention claimed is:

1. A compact gas sensor, comprising:
   a gas cell containing one or more gas species to be measured;
   a light emitter to emit light at one or more emission wavelengths including a characteristic wavelength for at least one of the one or more gas species and a reference wavelength, the light emitter disposed to emit the light through the gas cell and including:
   a continuous conductive layer that is heated to thermally emit the light;
   a dielectric layer formed over the continuous conductive layer; and
   a patterned conductive layer formed over the dielectric layer, the patterned conductive layer including a plurality of relief structures to define a layered light emitting structure that emits the reference wavelength at a first peak and the characteristic wavelength at a second peak;

a photodetector to generate a signal upon detection of the light emitted through the gas cell; and a computing device connected to the light emitter and the photodetector;

wherein the computing device receives, at a first time, the signal from the photodetector, the signal comprising a first signal corresponding to a light intensity at the reference wavelength at the first time;

wherein the computing device receives, at a second time, a second signal and a third signal from the photodetector, the second signal corresponding to a light intensity at the characteristic wavelength and the third signal corresponding to a light intensity at the reference wavelength at the second time; and wherein the computing device generates a calibrated second signal using the first signal and the third signal to measure a gas species from among the one or more gas species to compensate for a drift in the one or more emission wavelengths.

2. The gas sensor of claim 1, wherein the gas sensor is free of focusing or collimating optical elements.

3. The gas sensor of claim 1, wherein the patterned conductive layer comprises relief structures having a thickness in a range from 0.05 μm to 5 μm.

4. The gas sensor of claim 3, wherein the relief structures have a circular shape.

5. The gas sensor of claim 1, further comprising a broadband optical filter.

6. The gas sensor of claim 1, wherein the photodetector and the light emitter are integrated into a same substrate.

7. The gas sensor of claim 1 wherein the sensor is connected to an interface.

8. The gas sensor of claim 1 further comprising a memory to store sensor data.

9. The gas sensor of claim 1, wherein the patterned conductive layer comprises relief structures that have a radius in a range from 0.3 μm to 1.14 μm.

10. The gas sensor of claim 1, wherein the patterned conductive layer comprises relief structures that are organized in a supercell pattern including a first repeated short-range-order patch and a second repeated short-range-order patch.

11. The gas sensor of claim 10, wherein the first repeated short-range-order patch is characterized by a first lateral dimension and wherein the second repeated short-range-order patch is characterized by a second lateral dimension different than the first lateral dimension.

12. The gas sensor of claim 10, wherein the first repeated short-range-order patch generates light at the characteristic wavelength and the second repeated short-range-order patch generates light at the reference wavelength.

13. The gas sensor of claim 1 wherein the gas sensor is connected to a controller that controls delivery of a power signal to the light emitter.

14. The gas sensor of claim 13 wherein the controller is mounted on a printed circuit board with the emitter.

15. The gas sensor of claim 13 wherein the controller operates a heating cycle of the gas sensor.

16. The gas sensor of claim 13, wherein the computing device includes the controller.

17. The gas sensor of claim 1 wherein the emitted light includes a plurality of peaks having infrared wavelengths.

18. The gas sensor of claim 1 wherein the sensor measures concentrations of compounds within the one or more gas species.

19. The gas sensor of claim 1 further comprising a sensor interface circuit that connects the gas sensor and one or more additional sensors to a network.

20. The gas sensor of claim 1 wherein the patterned conductive layer has a periodic structure with a pitch that defines a separation between relief structures.

21. The gas sensor of claim 1, wherein the drift is caused by environmental effects.

22. The gas sensor of claim 1, wherein the drift is caused by thermal operation of the emitter.

23. The gas sensor of claim 1, wherein the drift further comprises drift of the detected signal of the photodetector.

24. The gas sensor of claim 1, wherein the computing device is configured to calibrate the gas sensor during thermal cycling of the emitter.

* * * * *